(12) United States Patent
Liu et al.

(10) Patent No.: US 12,426,844 B2
(45) Date of Patent: Sep. 30, 2025

(54) FIXTURING AND SUPPORT FOR MEDICAL IMAGING

(71) Applicant: Koning Corporation, Norcross, GA (US)

(72) Inventors: Shaohua Liu, Atlanta, GA (US); Ruola Ning, Atlanta, GA (US)

(73) Assignee: Koning Corporation, Norcross, GA (US)

( * ) Notice: Subject to any disclaimer, the term of this patent is extended or adjusted under 35 U.S.C. 154(b) by 0 days.

(21) Appl. No.: 18/914,206

(22) Filed: Oct. 13, 2024

(65) Prior Publication Data

US 2025/0032067 A1 Jan. 30, 2025

Related U.S. Application Data

(63) Continuation of application No. PCT/US2023/018344, filed on Apr. 12, 2023.
(Continued)

(51) Int. Cl.
*A61B 6/50* (2024.01)
*A61B 6/03* (2006.01)
(Continued)

(52) U.S. Cl.
CPC .............. *A61B 6/502* (2013.01); *A61B 6/032* (2013.01); *A61B 6/035* (2013.01); *A61B 6/0435* (2013.01); *A61B 6/0478* (2013.01); *A61B 6/0487* (2020.08); *A61B 6/4085* (2013.01); *A61B 8/0825* (2013.01); *G06T 7/00* (2013.01); *G06T 2207/30068* (2013.01)

(58) Field of Classification Search
CPC ..... A61B 6/0435; A61B 6/502; A61B 6/0414; A61B 6/032; A61B 90/17; A61B 5/708
See application file for complete search history.

(56) References Cited

U.S. PATENT DOCUMENTS 6,146,377 A 11/2000 Lee et al.
6,558,407 B1 5/2003 Ivanko et al.
(Continued)

FOREIGN PATENT DOCUMENTS

JP 2008/307234 A 12/2008
JP 2015112337 A * 6/2015 ............. A61B 6/032
(Continued)

OTHER PUBLICATIONS

Translation of JP-2015112337 (Year: 2015).*
Translation of JP-2018086198 (Year: 2018).*

*Primary Examiner* — David J Makiya
*Assistant Examiner* — Soorena Kefayati
(74) *Attorney, Agent, or Firm* — Bergman LLC; Michael Bergman

(57) ABSTRACT

A cone beam breast computed tomography system includes a breast stabilization unit with an internal surface region including a breast contact portion, where the breast contact portion serves to support a patient breast and maintain the position and stability of the breast during tomographic imaging. Certain removable breast stabilization units are received within a receiver of a patient interface panel of the cone beam breast computed tomography system, allowing selection and application of a breast stabilization unit compatible with the characteristics of a particular patient.

16 Claims, 15 Drawing Sheets

Related U.S. Application Data

(60) Provisional application No. 63/430,571, filed on Dec. 6, 2022, provisional application No. 63/401,475, filed on Aug. 26, 2022, provisional application No. 63/401,548, filed on Aug. 26, 2022, provisional application No. 63/401,513, filed on Aug. 26, 2022, provisional application No. 63/401,493, filed on Aug. 26, 2022, provisional application No. 63/401,546, filed on Aug. 26, 2022, provisional application No. 63/331,153, filed on Apr. 14, 2022.

(51) Int. Cl.
*A61B 6/04* (2006.01)
*A61B 6/40* (2024.01)
*A61B 8/08* (2006.01)
*G06T 7/00* (2017.01)

(56) References Cited

U.S. PATENT DOCUMENTS

| | | | |
|---|---|---|---|
| 6,987,831 B2 | 1/2006 | Ning | |
| 8,102,964 B2 | 1/2012 | Schilling et al. | |
| 10,039,511 B2 * | 8/2018 | Ito | A61B 6/502 |
| 2008/0187095 A1 * | 8/2008 | Boone | A61B 8/0825 378/37 |
| 2008/0230074 A1 * | 9/2008 | Zheng | A61B 5/055 128/869 |
| 2009/0054757 A1 * | 2/2009 | Noras | A61B 6/502 600/415 |
| 2009/0259122 A1 * | 10/2009 | Larson | G01R 33/30 600/564 |
| 2010/0067659 A1 * | 3/2010 | Bush | A61B 6/0435 378/68 |
| 2010/0069740 A1 * | 3/2010 | Larson | G01R 33/286 29/469 |
| 2010/0080350 A1 * | 4/2010 | Kalender | A61B 5/4312 378/65 |
| 2010/0086103 A1 * | 4/2010 | Jan | A61B 6/502 378/209 |
| 2018/0317867 A1 * | 11/2018 | Boone | A61B 6/0435 |
| 2018/0344167 A1 * | 12/2018 | Xiang | A61B 5/4312 |
| 2019/0046143 A1 * | 2/2019 | Cao | A61B 6/0435 |
| 2019/0175123 A1 * | 6/2019 | Ohtani | A61B 6/4057 |
| 2021/0219933 A1 | 7/2021 | Boone et al. | |

FOREIGN PATENT DOCUMENTS

| | | |
|---|---|---|
| JP | 2018086198 A * | 6/2018 |
| WO | WO2017/091787 A1 | 6/2017 |
| WO | WO2017/180570 A1 | 10/2017 |
| WO | WO2019/221899 A1 | 11/2019 |

* cited by examiner

FIXTURING AND SUPPORT FOR MEDICAL IMAGING

CROSS-REFERENCE TO RELATED APPLICATIONS

The present application is a continuation of PCT patent application PCT/US2023/018344 filed on Apr. 12, 2023, which claims the benefit of provisional patent applications OMNIBUS DISCLOSURE, set forth in an application for Letters Patent of the United States already filed on Apr. 14, 2022 as U.S. Provisional Application No. 63/331,153, and FIXTURING AND SUPPORT FOR MEDICAL IMAGING, set forth in an application for Letters Patent of the United States already filed on Aug. 26, 2022 as U.S. Provisional Application No. 63/401,475, and ERGONOMIC IMPROVEMENTS IN CONE BEAM BREAST COMPUTED TOMOGRAPHY, set forth in an application for Letters Patent of the United States already filed on Aug. 26, 2022 as U.S. Provisional Application No. 63/401,493, and STATIONARY DETAIL IMAGING IN CONE BEAM BREAST COMPUTED TOMOGRAPHY, set forth in an application for Letters Patent of the United States already filed on Aug. 26, 2022 as U.S. Provisional Application No. 63/401,513, and CONE BEAM BREAST COMPUTED TOMOGRAPHY WITH PATIENT SUPPORT SUBSYSTEM, set forth in an application for Letters Patent of the United States already filed on Aug. 26, 2022 as U.S. Provisional Application No. 63/401,546, and, CONE BEAM BREAST COMPUTED TOMOGRAPHY WITH PIVOTAL GANTRY SUBSYSTEM, set forth in an application for Letters Patent of the United States already filed on Aug. 26, 2022 as U.S. Provisional Application No. 63/401,548, and ULTRASONIC HYBRID IMAGING IN CONE BEAM BREAST COMPUTED TOMOGRAPHY, set forth in an application for Letters Patent of the United States already filed on Dec. 6, 2022 as U.S. Provisional Application No. 63/430,571, the disclosures of all of which are herewith incorporated by reference in their entireties.

FIELD OF THE INVENTION

The present invention relates to the field of cone beam tomographic imaging, and in particular to the field of breast stabilization in tomographic imaging.

SUMMARY

According to the National Cancer Institute, one out of eight women will be diagnosed with breast cancer in her lifetime. And while a reduction in mortality from breast cancer is evident in published reports, each year 40,000 women will die of the disease.

The optimal breast imaging technique detects tumor masses when they are small, preferably less than 10 mm in diameter. It is reported that 93% of women with mammographically detected invasive breast carcinoma 1-10 mm have a 16-year survival rate. In addition, as the diameter of the tumor at detection decreases, the probability of metastasis declines sharply. If a breast tumor is detected when it is 10 mm or less, the probability of metastasis will be equal to 7.31%. If a 4 mm carcinoma is detected, the metastatic probability will be decreased by more than a factor of 10, to 0.617%.

Mammography, which on average can detect cancers about 12 mm in size, was the most effective tool for the early detection of breast cancer until the advent of cone beam breast computed tomography. Mammography has relatively low sensitivity to small breast cancers (under several millimeters). Specificity and the positive predictive value of mammography remain limited owing to structure and tissue overlap. The limited sensitivity and specificity in breast cancer detection of mammography are due to its poor contrast detectability, which is common for all types of projection imaging techniques (projection imaging can only have up to 10% contrast detectability), and mammography initially detects only 65-70% of breast cancers. The sensitivity of mammography is further reduced to as low as 30% in the dense breast. Digital mammography (DM) was developed to try to overcome the limitations inherent in screen-film mammography (SFM) by providing improved contrast resolution and digital image processing; however, a large-scale clinical trial, the Digital Mammographic Imaging Screening Trial (DMIST), showed that the rates of false positives for DM and SFM were the same.

The relatively low specificity of mammography leads to biopsy for indeterminate cases, despite the disadvantages of added cost and the stress it imposes on patients. Nearly 80% of the over one million breast biopsies performed annually in the U.S. to evaluate suspicious mammographic findings are benign, burdening patients with excessive anxiety and the healthcare system with tremendous cost. There is a need for more accurate characterization of breast lesions in order to reduce the biopsy rate and the false-positive rate of pre-biopsy mammograms.

To address the mammography limitations as indicated above, one of the inventors has previously developed a cone beam breast CT (CBBCT). Briefly, the major features of CBBCT include a horizontal, ergonomically designed patient table with a modular insert to optimize coverage of the uncompressed breast, including the chest wall; wide openings (1 m) on each side of the patient table for easy access to the breast for positioning and potentially good access for imaging-guided biopsy and other procedures without significantly changing the basic platform; and slip-ring technology that facilitates efficient dynamic contrast imaging studies and angiogenesis imaging in the future.

The results of phantom studies indicate that CBBCT can achieve a spatial resolution up to about 2.8 lp/mm, allowing detection of a 2 mm carcinoma and microcalcifications about 0.2 mm in size for an average size breast (about 13 cm in diameter at the chest wall) with a total dose of about 5 mGy. This dose is less than that of a single mammography exam, assuming two views are required for each breast. The image quality of CBBCT for visualizing breast tissues, breast tumors and calcifications is excellent, and coverage of the breast, including the chest wall region, is at least equivalent to mammography. Visualization of major blood vessels is very good without using a contrast agent.

Accordingly, CBBCT offers significant improvement in detecting and biopsying suspected lesions in a patient. Further, in many procedures using CBBCT, an image can be acquired without requiring the compression of the breast tissue universally associated with mammography. The compressive breast fixturing apparatus used in mammography is widely considered to be uncomfortable, and is often cited as a factor that discourages patients from seeking otherwise desirable breast cancer screenings. Additional improvements in CBBCT imaging offer the potential to expand on these benefits. In light of the foregoing, the ability to perform improved CBBCT imaging without resorting to the uncomfortable breast fixation associated with mammography would be highly desirable.

In current practice, a patient undergoing CBBCT lies prone on a table. A subject breast is disposed downward through an aperture in an upper surface of the table, depending from the chest wall into an imaging chamber disposed under the table. The position of the breast within the imaging chamber is maintained by stasis of the patient (i.e., keeping the patient stationary) as the patient lies on an upper surface of the table.

An imaging apparatus is coupled to a mobile gantry which is supported on a bearing device for rotation about an axis of rotation. The axis of rotation is disposed in a generally vertical orientation and passes through the aperture in the upper surface of the table. Preferably, an approximate centroid of the breast to be imaged is arranged such that the axis of rotation passes through the approximate centroid.

During imaging, the mobile gantry rotates around the axis of rotation, bringing the imaging apparatus through at least a portion of a circular path. As it traverses this path, the imaging apparatus emits a series of x-ray pulses and captures corresponding image data which is processed to prepare a tomographic model of the breast.

To avoid blurring during individual x-ray pulses, and to maintain consistency of images between the pulses, the patient remains stationary during imaging. Even small variations in spatial positioning of the breast can result in reduced image clarity.

In existing CBBCT systems, the breast hangs freely within the imaging chamber, or is captured in a compressive system that squeezes the breast tissue and/or provides a spatial fixturing in anticipation of biopsy related activities. The compressive system can be uncomfortable, and the freely hanging breast is subject to motions and vibrations that, as noted above, can have a detrimental effect on image quality.

Existing fixturing apparatus for other applications of cone beam computed tomography, such as bite-sticks used in dental tomography are inapposite to the present problem.

The inventors of the present invention having given long and careful consideration to the problems associated with CBBCT imaging (and, in particular, to the need to stabilize a CBBCT subject for effective imaging), have developed new and useful systems, apparatus and methods that represent a substantial improvement over previously known approaches. The present invention includes apparatus, and corresponding systems and methods, for the support and fixturing of tissue during tomographic imaging and, in particular embodiments, for use in CBBCT.

In certain embodiments, the invention includes a breast support apparatus. In certain embodiments, the breast support apparatus includes a stabilizer unit and a positioning apparatus coupled to the stabilizer unit so as to provide adjustable positioning of the stabilizer unit with respect to a reference frame of the tomographic imager.

In certain embodiments, the stabilizer unit includes a generally rigid body having a primary surface region configured to be disposed in contact with a corresponding surface region of a subject breast. In selected embodiments, the generally rigid body includes a material selected for a desirable level of transparency with respect to an operative wavelength of imaging energy. Accordingly, in certain embodiments, the generally rigid body includes one or more of expanded polystyrene; polystyrene; polyethylene; Acrylonitrile Butadiene Styrene (ABS); polypropylene; acrylics (e.g., polymethyl methacrylate); polyamide; polyaramid; aerogels; ceramics; fiber reinforced composites; and polycarbonate (e.g., Lexan®), among others.

The following description is provided to enable any person skilled in the art to make and use the disclosed inventions and sets forth the best modes presently contemplated by the inventors of carrying out their inventions. In the following description, for purposes of explanation, numerous specific details are set forth in order to provide a thorough understanding of the present invention. It will be apparent to one skilled in the art, however, that the present invention may be practiced without these specific details. In other instances, well-known structures and devices are shown in block diagram form in order to avoid unnecessarily obscuring the substance disclosed. These and other advantages and features of the invention will be more readily understood in relation to the following detailed description of the invention, which is provided in conjunction with the accompanying drawings.

It should be noted that, while the various figures show respective aspects of the invention, no one figure is intended to show the entire invention. Rather, the figures together illustrate the invention in its various aspects and principles. As such, it should not be presumed that any particular figure is exclusively related to a discrete aspect or species of the invention. To the contrary, one of skill in the art will appreciate that the figures taken together reflect various aspects and embodiments exemplifying the invention.

Correspondingly, reference throughout the specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" in various places throughout the specification are not necessarily all referring to the same embodiment. Furthermore, the particular features, structures, or characteristics may be combined in any suitable manner in one or more embodiments.

DETAILED DESCRIPTION

The following description is provided to enable any person skilled in the art to make and use the disclosed inventions and sets forth the best modes presently contemplated by the inventors of carrying out their inventions. In the following description, for purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the substance disclosed.

It should be noted that while any of the embodiments described for exemplary purposes below will identify specific elements and combinations of elements, these examples are not intended to be determinative. Rather, discrete elements will, in appropriate circumstances, be combined into integral elements and/or assemblies. Further, the present disclosure of aspects and features of particular elements described herewith as integral, should be understood to convey also the disclosure of individual elements and assemblies providing the same characteristics and/or functionality.

Figure 1:
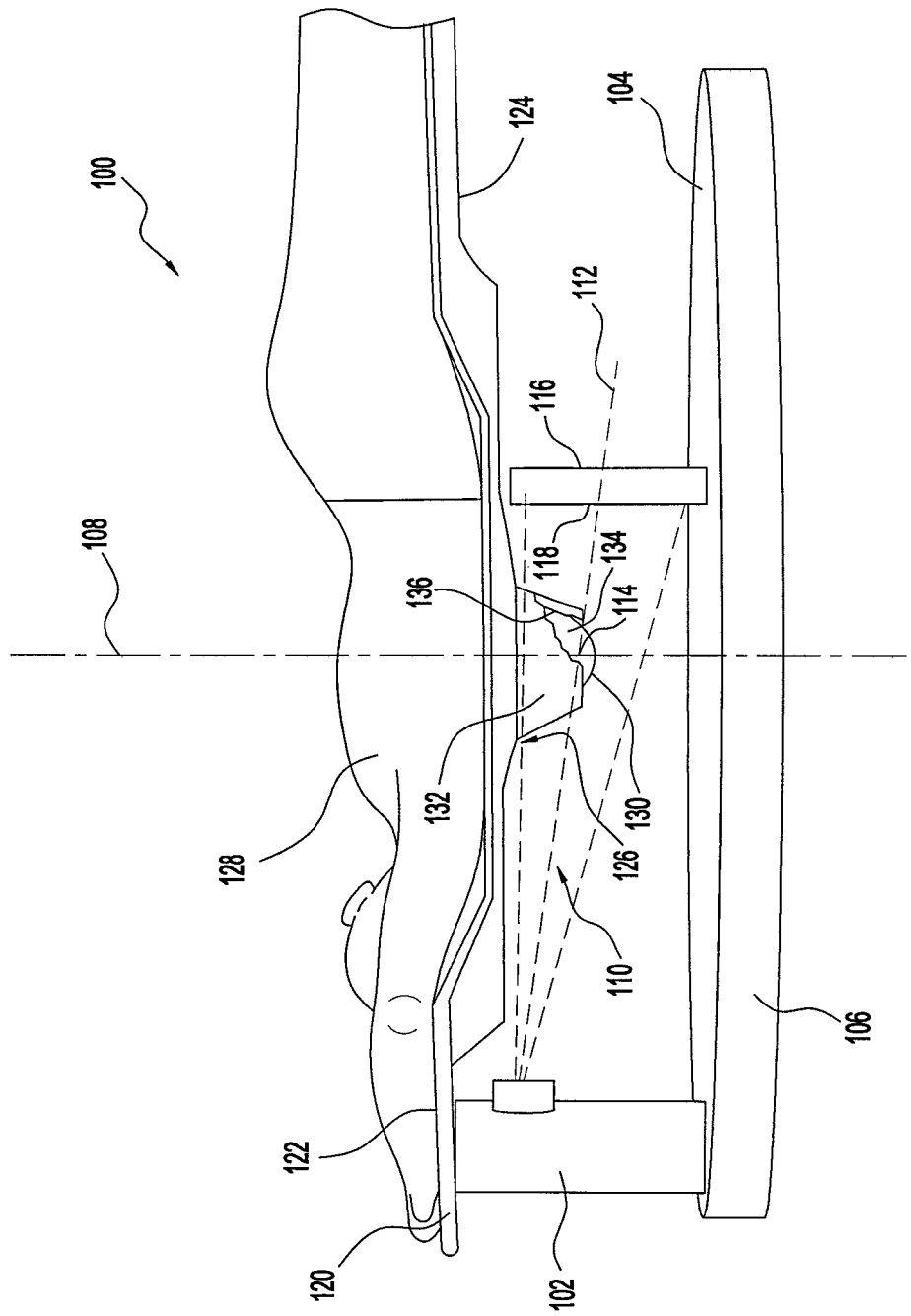
FIG. 1 shows in schematic cutaway perspective view a portion of a CBBCT breast imaging system including an exemplary breast stabilizer unit.

FIG. 1 shows, in cutaway perspective view, a portion of an exemplary CBBCT imaging system 100 including a breast support apparatus, prepared according to principles of the invention. The system 100 includes an x-ray source 102. The x-ray source 102 is mounted on an upper surface 104 of a rotating gantry 106. The rotating gantry 106 is supported by a bearing, and arranged for rotation about an axis of rotation 108.

The x-ray source 102 is configured to emit a beam of x-rays 110. The beam of x-rays 110 defines a beam longitudinal axis 112 that, in the illustrated embodiment, intersects (at 114) the axis of rotation 108.

In certain embodiments of the invention, beam 110 is configured as a cone beam. In certain configurations, a cross-section of the beam 110 taken transverse to the longitudinal axis 112 defines a disk of substantially uniform x-ray intensity with a substantially circular perimeter.

In other configurations within the scope of the invention, a cross-section of the beam 110 taken transverse to the longitudinal axis 112 defines a region of substantially uniform x-ray intensity with a substantially circular perimeter save for a portion of the disc outwardly of a chord of said circular perimeter. As will be appreciated on consideration of the further disclosure below, in certain embodiments, the chord will be disposed in generally parallel spaced relation to a lower surface of a patient table.

In still further configurations within the scope of the invention, a cross-section of the beam 110 taken transverse to the longitudinal axis 112 defines a region of substantially uniform x-ray intensity with a polygonal perimeter, where the polygonal perimeter will, in respective embodiments and configurations, include any of the triangular perimeter, a square perimeter, a pentagonal perimeter, a hexagonal perimeter, a perimeter of any higher geometric shape, and a perimeter having any arbitrary curve or combination of line segments and curves according to the demands of a particular application. Moreover, it will be appreciated that any of the cross-sectional configurations described above may define a beam having a nonuniform intensity including, without limitation an intensity that falls to zero in certain regions of the cross-section.

An x-ray detector 116 is also mounted on the upper surface 104 of the rotating gantry 106. In one exemplary embodiment, the x-ray detector 116 includes a flat panel detector having a generally planar receiving surface 118. Receiving surface 118 is disposed generally transverse to longitudinal axis 112 and on the opposite side of axis of rotation 108 from the x-ray source 102.

Rotation of the gantry 106 about axis of rotation 108 during operation of the imaging system 100 will result in the receiving surface 118 following a transit path about axis of rotation 108. In a typical configuration, the transit path will include at least a portion of a circle disposed transverse to, and centered at, axis of rotation 108. It should be noted, however, that other transit paths (however achieved) are considered to be within the scope of the invention, and to be disclosed herewith.

In certain embodiments of the invention, one or both of the x-ray source 102 and the x-ray detector 116 are arranged so that their respective positions on the upper surface 104 of gantry 106 are adjustable. For example, the x-ray source 102 and the x-ray detector 116 may be adjustable in a radial direction with respect to axis of rotation 108, in a circumferential direction with respect to axis of rotation 108, in a direction towards or away from gantry surface 104, or in any other orientation or manner deemed beneficial by the designer or user of a particular apparatus embodying the invention.

A patient table 120, otherwise known as a patient interface panel, includes an upper surface 122 and a lower surface 124. An aperture 126 communicates between the upper surface 122 and lower surface 124 of the table. The upper surface 122 is arranged to support a patient 128, typically with the patient lying prone on upper surface 122, as illustrated. In this arrangement, a breast 130 of the patient is disposed pendant from the patient's chest wall downwardly through aperture 126.

In the illustrated embodiment, a breast stabilizer unit 132 (shown in cutaway view) is disposed at aperture 126, and extending below table surface 124. At least a portion of an external surface region 134 of breast 130 is disposed in contact with an internal circumferential surface 136 of stabilizer unit 132.

As will be further discussed below, breast stabilizer unit 132 is coupled and supported within the imaging system 100 so as to maintain the stabilizer unit substantially spatially fixed (i.e., immobile) with respect to axis of rotation 108 during imaging of the breast 130. In certain applications, the breast stabilizer unit 132 is configured and adjusted to maintain an approximate geometric centroid of the breast in an intersection with axis of rotation 108.

In further applications, the breast stabilizer unit 132 is configured and adjusted to maintain an approximate geometric centroid of the breast coincident with intersection 114 of axis of rotation 108 and longitudinal axis 112 of the x-ray beam. It will be appreciated by one of skill in the art, however, that any of a wide variety of placements and configurations of the breast will be desirable in respect to a particular patient, application, or imaging objective, and will be achieved by an appropriate shape, configuration, and placement of the breast stabilizer unit 132.

Accordingly, the breast stabilizer unit 132 is arranged, adapted and configured to support, stabilize and hold in place, at least a portion of breast 130, with respect to the above-described transit path of imaging surface 118, during imaging of the breast by imaging system 100.

As will be further discussed below, a variety of different arrangements are well suited to maintaining breast stabilizer unit 132 substantially stable and immobile with respect to imaging system 100 during imaging. For example, according to certain aspects of the invention, the breast stabilizer unit 132 can be supported from above, from below, from a side, or in any other manner considered beneficial and/or consistent with the requirements of a particular system, application, patient or imaging modality.

These various arrangements will be employed individually and/or in combination depending on the specific requirements of a particular application, and the use of one arrangement should not be presumed to preclude the concurrent use of another arrangement or modality. Accordingly, it will be understood that the configurations discussed below are merely exemplary of a variety of devices and arrangements, including combinations of such devices and arrangements, that will be clear to the practitioner of ordinary skill in the art in light of the present disclosure.

Figure 2:
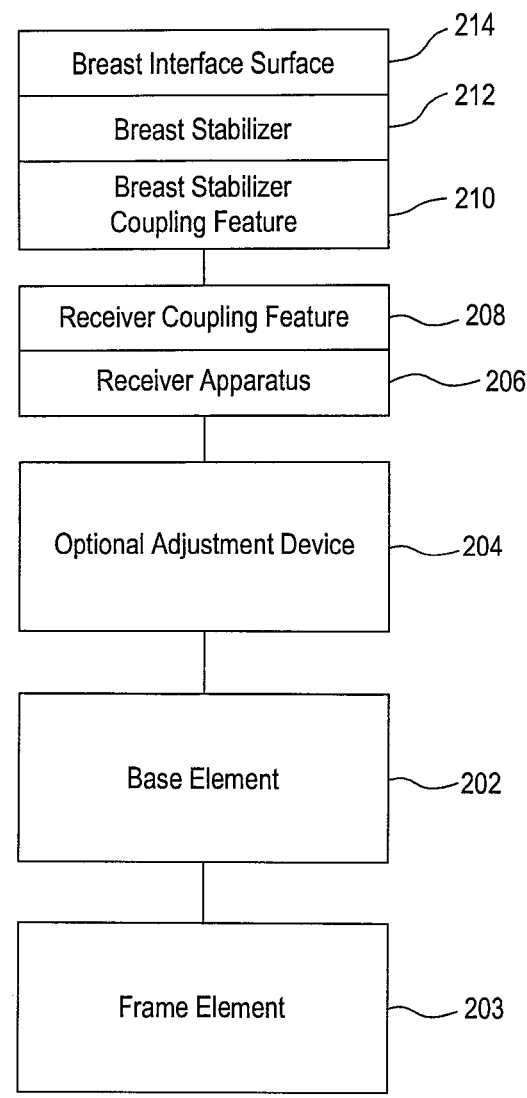
FIG. 2 shows in block diagram form the structural relationship of certain aspects of an exemplary CBBC T breast imaging system prepared according to principles of the invention.

FIG. 2 shows, in schematic block diagram form, a fixturing subsystem 200 of an exemplary CBBCT imaging system for breast support and fixturing prepared according to principles of the invention (like, e.g., imaging system 100 above). As illustrated, the subsystem 200 is supported by a base element 202 of the imaging system. In certain exemplary embodiments, the base element is coupled to a frame element 203 of the breast imaging system (where the frame element is a structural element supporting various components of the imaging system, e.g., a foundation element), or directly supported on the floor of a room in which the breast imaging system is disposed. Direct floor support offers certain advantages inasmuch as, being discretely supported, the base element 202 may be relatively isolated from certain vibrations that might otherwise be present in the breast imaging system.

The base element 202 is operatively coupled to an adjustment device 204. Adjustment device 204 is arranged and configured to permit adjustment of the spatial location of a breast stabilizer 212, as discussed below, with respect to, for example, an imaging region between an x-ray source and detector of a breast imaging system. Accordingly, in certain embodiments, adjustment device 204 is adapted to adjust an elevation of a portion of the breast with respect to the base element and, hence, with respect to the transit path and imaging region referenced above.

As illustrated, a receiver apparatus 206 is operatively coupled to the adjustment device 204. The receiver apparatus 206 includes a body portion and/or a support member. In certain embodiments, the receiver apparatus 206 includes a receiver coupling feature 208.

The receiver coupling feature 208 includes at least one surface region that is geometrically complementary to a corresponding surface region of a coupling feature 210 of a breast stabilizer unit 212. Consequently, in certain embodiments, the coupling feature 210 of the breast stabilizer unit 212 can be operatively coupled to the coupling feature 208 of the receiver apparatus. When applied, this coupling serves to maintain the breast stabilizer unit 212 in a substantially fixed spatial relation (i.e., immobile) to the receiver apparatus 206.

In addition, the coupling between the breast stabilizer unit 212 and the receiver apparatus 206 allows the subject breast to be maintained in a defined relationship to the base element 202. Depending on the arrangement and configuration of the adjustment device 204, this defined relationship will be controllable by adjustment prior to imaging, and/or by active positioning of the position and orientation of the receiver apparatus with respect to the base element during the imaging process.

As will be further discussed below, the breast stabilizer unit 212 is configured to support the breast of a patient in a manner that positions and stabilizes the breast for imaging. Accordingly, in certain embodiments of the invention, the breast stabilizer unit 212 will include an interface surface region 214. When in use, a surface region of the patient's breast is supported, directly or indirectly, on the interface surface region 214. In certain embodiments of the invention, the interface surface region includes a continuous circumferential surface region of the breast stabilizer unit disposed about a longitudinal axis of the breast. In certain embodiments of the invention, the interface surface region defines a substantially circumferentially continuous portion of a substantially conical (or cylindrical, ellipsoidal, parabolic or other) surface region such that the interface surface region is disposed in contact with a substantially continuous circumferential region of the patient breast.

In certain embodiments, the interface surface region forms a substantially closed surface region downwardly of an upper peripheral edge of the breast stabilizer unit 212 such that the breast is stabilized and supported from below by a transverse surface region of the breast stabilizer unit 212 disposed transverse to a longitudinal axis of the breast. In certain embodiments of the invention, the transverse surface region is substantially continuous with the balance of the internal surface region such that the entirety of the breast stabilizer unit 212 internal surface region is substantially continuous and/or coterminous. In certain embodiments of the invention, the internal surface region is maintained substantially immobile with respect to the patient interface panel, except for any elastic compliance including, for example, to improve patient comfort and/or conformance to breast geometry.

As discussed above, the adjustment device 204 is configured and adapted to adjust an elevation of the breast stabilizer unit 212, and the breast that it contains, in at least a vertical degree of freedom. In other embodiments of the invention, the adjustment device 204 will provide adjustment in additional degrees of freedom such as pitch, yaw, and roll taken with respect to a longitudinal axis of the breast.

Operation of the adjustment device 204 will, in certain embodiments of the invention, the undertaken by a manual adjustment of a manual actuator such as, and merely for example, a knob/screw combination, or by a ratcheting jack mechanism. In other embodiments of the invention, adjustment will be by simple manual motion of the adjustment device, displacing respective frictional surfaces with respect to one another. Thus, for example, a helically wound "gooseneck tube," as known in the art (or, a plurality of gooseneck tubes, e.g. three gooseneck tubes in a tripod configuration), will be included to provide the requisite manual/frictional adjustment.

It will be noted that in certain embodiments of the invention, the breast stabilizer 212 will be placed in its desired position and orientation prior to the breast to be imaged being disposed adjacent to the internal surface region of the breast stabilizer 212.

In other embodiments of the invention, the breast to be imaged will be disposed within the breast stabilizer and, thereafter, the position and orientation of the breast stabilizer 212 will be adjusted. In certain embodiments of the invention, the breast will be placed within and coupled to the breast stabilizer and, thereafter, the breast stabilizer will be coupled to the receiver apparatus and the adjustment device will be thereafter operated to finalize positioning of the breast, which is pre-positioned within the breast stabilizer.

It should be noted that, in certain embodiments of the invention, adjustments to the adjustment device will be made on a plurality of occasions, both before and after the breast is placed within the breast stabilizer device 212 and, in some embodiments, both before and after the breast stabilizer device is coupled to the receiver apparatus.

It should be noted that, in certain embodiments, the adjustment device 204 is omitted, and the receiver apparatus 206 is coupled directly to the base element 202. In such an arrangement, where adjustment of the position of the breast is desirable, the size or other configuration of the breast stabilizer unit 212 may be selected to provide the desired breast location. Accordingly, in certain embodiments of the invention, the adjustment device 204 described above may be omitted, and other arrangements made to provide for a desirable positioning of the breast with respect to an imaging apparatus.

Figure 3A:
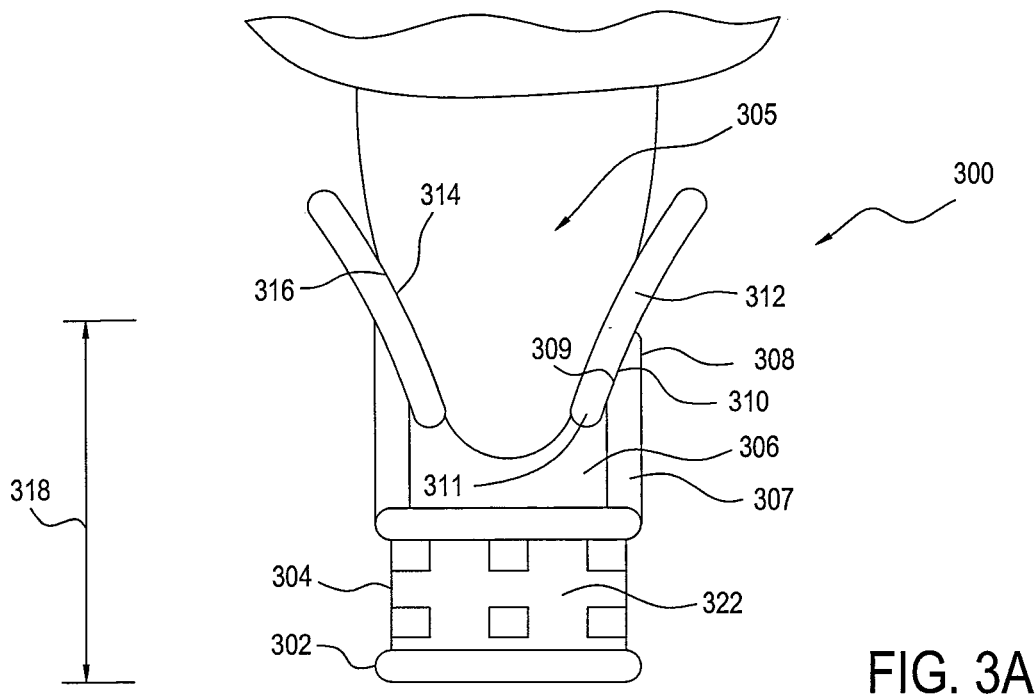
FIG. 3A shows in schematic cross-section, certain aspects of an exemplary CBBCT breast imaging system including a breast stabilizer unit prepared according to principles of the invention in a first exemplary configuration.

Referring now to FIG. 3A, a breast support subsystem 300 (exemplary of subsystem 200 described above) is supported by a base element 302 of the imaging system. In certain exemplary embodiments, the base element is coupled to a frame (or frame element) of the breast imaging system, or directly supported on the floor of a room in which the breast imaging system is disposed. As discussed above, direct floor support offers certain advantages inasmuch as, being discretely supported, the base element 302 may be relatively isolated from certain vibrations that might otherwise be present in the breast imaging system.

The base element 302 is operatively coupled to an adjustment device 304. Adjustment device 304 is arranged and configured to permit adjustment of the spatial location of a subject breast 305 with respect to, for example, an imaging region between an x-ray source and detector of a breast imaging system. Accordingly, in certain embodiments, adjustment device 304 is adapted to adjust an elevation 318 of a portion of the breast 305 with respect to the base element 302 and with respect to the imaging region referenced above.

As illustrated, a receiver apparatus 306 is operatively coupled to the adjustment device 304. The receiver apparatus 306 includes a body portion and/or a support member 307. In certain embodiments, the receiver apparatus 306 includes a receiver coupling feature 308. The receiver coupling feature 308 includes at least one surface region 309 that is geometrically complementary to a corresponding surface region 310 of a coupling feature 311 of a breast stabilizer unit 312.

Consequently, in certain embodiments, the coupling feature 311 of the breast stabilizer unit 312 can be operatively coupled to the coupling feature 308 of the receiver apparatus 306. When applied, this coupling serves to maintain the breast stabilizer unit 312 immobile (i.e., in a substantially fixed spatial relationship) with respect to the receiver apparatus 306.

In addition, the coupling between the breast stabilizer unit 312 and the receiver apparatus 306 allows the subject breast 305 to be maintained in a defined spatial relationship to the base element 302. Depending on the arrangement and configuration of the adjustment device 304, this defined relationship will be controllable by adjustment prior to imaging, and/or by active positioning of the position and orientation of the receiver apparatus with respect to the base element during the imaging process.

As will be further discussed below, the breast stabilizer unit 312 is configured to support the breast of a patient in a manner that positions and stabilizes the breast for imaging. Accordingly, in certain embodiments of the invention, the breast stabilizer unit 312 will include an interface surface region 314. When in use, a surface region 316 of the patient's breast 305 is supported, directly or indirectly, on the interface surface region 314. As will be understood in light of the foregoing, once the breast stabilizer unit is installed, the interface surface region is maintained substantially immobile with respect to the patient interface panel, neglecting any elastic compliance provided, for example, to improve patient comfort and/or conformance to breast geometry.

Figure 3B:
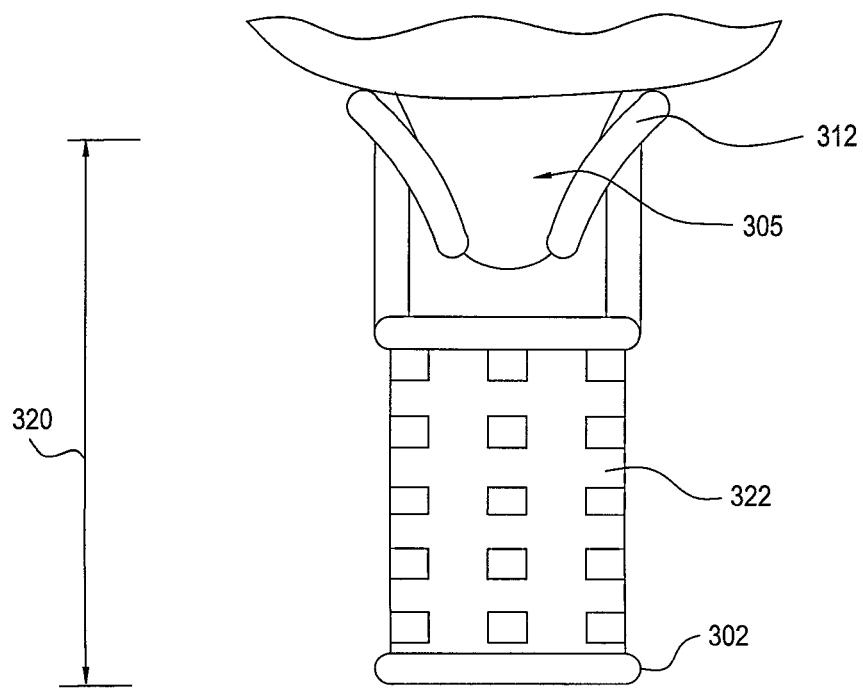
FIG. 3B shows in schematic cross-section, certain aspects of an exemplary CBBCT breast imaging system including a breast stabilizer unit prepared according to principles of the invention in a second exemplary configuration.

Referring now to FIG. 3B, one sees that a height of the breast stabilizer unit 312 above the base element 302 can be adjusted between a first relatively low retracted height 318 and a second relatively high extended height 320. Correspondingly, the location of the subject breast 305 is adjusted, and position for imaging in accordance with the requirements of a particular imaging process, diagnostic, patient or procedure.

It should be noted that, in certain embodiments, the adjustment device 304 is omitted, and the receiver apparatus 306 is coupled directly to the base element 302. In such an arrangement, where adjustment of the position of the breast is desirable, the size or other configuration of the breast stabilizer unit 312 may be selected to provide the desired breast location.

In such circumstances, a patient imaging kit may include, for example, a variety of breast stabilizer units of various sizes. Such a kit will be employed in a method, according to certain embodiments of the invention, wherein a particular appropriately sized breast stabilizer unit 312 is selected, according to parametric measurements of the breast to be imaged, from a plurality of breast stabilizer units contained within the kit.

In other embodiments, breast stabilizer units of various shapes and sizes may be provided in discrete packaging, and received in quantity, such that a particular breast stabilizer unit may be selected from a local inventory according to the requirements of a particular imaging event or procedure.

It will be appreciated by one of skill in the art that it will be beneficial, in certain aspects of the invention, to provide visual indicia as to the size, shape, and/or other characteristics of a particular breast stabilizer unit. Thus, for example, breast stabilizer units may be color-coded, bear printed or molded indicia as to size and shape, bear a label or printed indicia in the form of conventional numerals, whether Arabic, Roman, or otherwise, and/or include machine-readable indicia such as, for example and without limitation, a Barcode, QR code or RFID tag or the like. Of course, it will be appreciated by one of skill in the art that any combination of the foregoing will also be used in an appropriate application of the invention.

In certain embodiments of the invention, a dispenser unit will be provided including storage and dispensing apparatus. The dispenser unit will be adapted to provide an appropriately sized and shaped breast stabilizer unit to medical personnel upon the entry of appropriate information at a data interface of the dispensing apparatus.

In certain embodiments of the invention, the data interface will be a human user interface, such as a keyboard, keypad, and/or touchscreen, in any configuration known, or that becomes known, in the art. In other embodiments of the invention, automatic measuring apparatus will determine the requisite appropriate information and provide the same to the data interface. In still other embodiments of the invention, information from a patient record, whether paper or electronic, will be received by the data interface and employed in the consequent dispensing of one or more breast stabilizer units.

In still other embodiments, an individualized breast stabilizer unit will be prepared in situ by, for example, a molding process, a wrapping process, or a 3D printing process or other additive process, a laser machining process or other subtractive process, (or some combination thereof) according to parametric measurements of the subject breast, and the requirements of a particular imaging specification. Thus, in certain aspects, the invention will include a method of stabilizing a breast for CBBCT scanning that includes preparing said individualized breast stabilizer unit by forming the breast stabilizer unit with an additive process such as one or more of a 3D printing laser sintering process, a 3D printing photopolymer curing process, a 3D printing melt thermopolymer process, a 3D printing catalytic thermoset process, and combinations thereof. Likewise, in further aspects, the invention will include a method of stabilizing a breast for CBBCT scanning backspace that includes preparing the individualized breast stabilizer unit by forming the breast stabilizer unit with a subtractive process including one or more of a laser machining process, a mechanical milling process, an electrical discharge milling process, a chemical milling process, and combinations thereof.

Accordingly, in certain embodiments of the invention, the adjustment device 304 described above may be omitted, and other arrangements made to provide for a desirable positioning of the breast with respect to an imaging apparatus.

As represented in FIGS. 3A and 3B, an extension mechanism 322 within the adjustment device 304 provides for the indicated adjustment action of the adjustment device. As will be appreciated by one of skill in the art, the extension mechanism 322 can be implemented with a wide variety of actuators. For example, in certain embodiments, the extension mechanism will include one or more of a rack and pinion apparatus, an Acme screw and Acme nut; a ballscrew assembly; a linear stepping motor; paired transverse complementary ramps; a pneumatic cylinder; a pneumatic bladder; a pneumatic bellows; a hydraulic cylinder; a hydraulic bladder; a hydraulic bellows; a scissors linkage mechanism, including, for example, a scissors linkage mechanism linkage operated by a lead screw, a cylinder, or any of the other actuators discussed herewith, or any other appropriate actuator; a sarrus linkage mechanism; a thermoelectric actuator; a shape memory alloy actuator; a cable and pulley arrangement; a compressive spring; a tension spring; a torsion spring; a coil spring; an assembly of leaf springs; a spring including a plurality of Belleville washers; a ratcheting lift jack mechanism; a crease pattern deployable actuator; or any other linear actuator currently known, or that becomes known in the art, that is suited to the requirements of a particular application and to providing the requisite extension function.

Figure 4A:
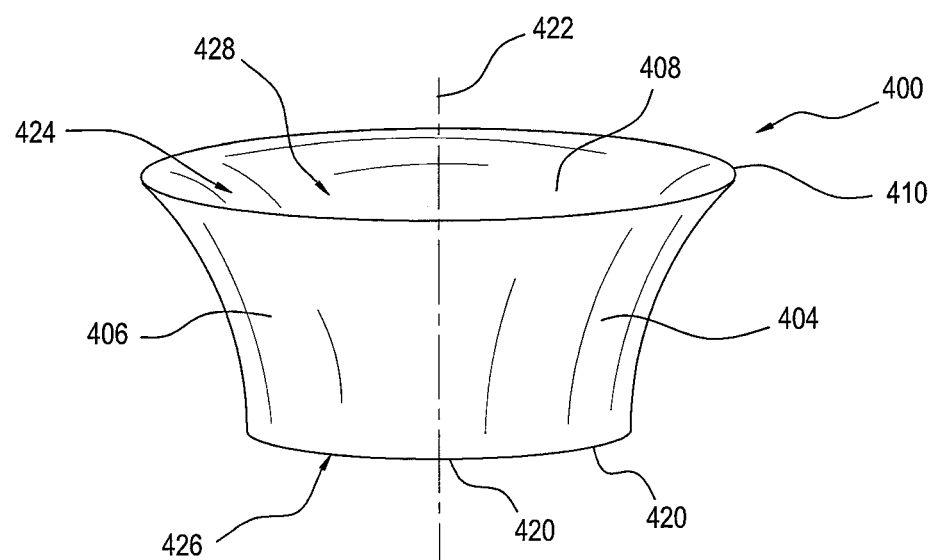
FIG. 4A shows in schematic perspective view, certain aspects of an exemplary CBBCT breast imaging system including a breast stabilizer unit prepared according to principles of the invention.

FIG. 4A shows, in schematic perspective view, further aspects of a breast stabilizer unit 400 prepared according to principles of the invention. One of skill in the art will appreciate that illustrated breast stabilizer unit 400 will, in a particular embodiment and without limitation, be exemplary of any of breast stabilizer units 132, 212, 312 as described above, or any other breast stabilizer unit described or implied herewith.

Figure 4B:
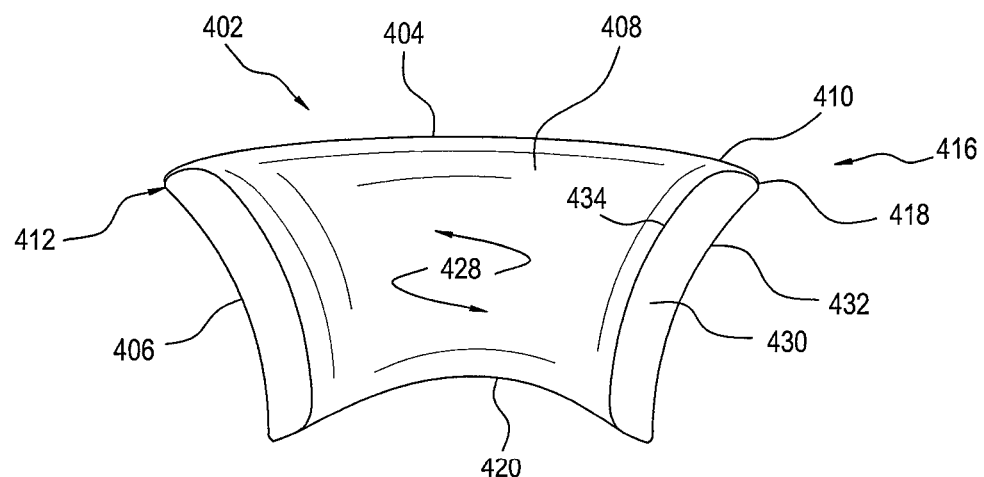
FIG. 4B shows in schematic cutaway perspective view, certain aspects of an exemplary CBBCT breast imaging system including a breast stabilizer unit prepared according to principles of the invention.

FIG. 4B shows a portion 402 of the breast stabilizer unit 400 in cutaway schematic perspective view, further illuminating the shape and characteristics of the device exemplified herewith. Accordingly, FIGS. 4A and 4B are herewith considered concurrently.

Exemplary breast stabilizer unit 400 includes a body portion 404. The body portion 404 has an external surface region 406 and an internal surface region 408. In the illustrated embodiment, the external surface region 406 and internal surface region 408 meet at a generally circular upper circumferential region 410.

It should be noted that circumferential region 410 is designated an "upper" circumferential region only for ease of discussion. In actual practice, the breast stabilizer unit 400, and any apparatus described herewith, will assume any orientation and position considered desirable for a particular application, function or modality of use.

Likewise, while the illustrated circumferential region 410 is indicated to be generally circular, it should be understood that this is merely exemplary of a wide variety of geometric shapes that may be deemed appropriate to a particular application of the invention, all of which are considered to be within the scope of the present disclosure. Accordingly, in certain embodiments, circumferential region 410 will have a generally elliptical form, a generally oval form, a flat oval form, a polygonal form, including (without limitation), for example, a generally triangular form, a generally rectangular form (including without limitation, for example, a generally square form), a pentagonal form, a hexagonal form, or any higher order polygonal form, a poly-arcuate form including, for example, two or more chordally intersecting circular arcs, or any combination of curves and/or line segments that may be deemed desirable.

Similarly, internal surface region 408 will have any form deemed desirable in relation to a particular patient or procedure. As such, and merely by way of example, respective embodiments of the invention will include an internal surface region having the characteristics (including partial characteristics) of a generally planar portion, a generally cylindrical portion, the cylinder having any circular or other cross-section, a generally toroidal portion, a generally spherical portion (including hemispherical or any fraction thereof), a generally ellipsoidal portion, a generally paraboloid portion, a generally hyperbaloid portion, an elliptic parabola portion, a parabola of revolution portion, a generally hyperbolic parabola portion, a generally conical portion, a generally sinusoidal portion, a generally synclastic portion, a generally anti-clastic portion, a generally planar portion having any peripheral configuration, and any other geometric shape deemed to be beneficial in some respect in relation to improving imaging, patient comfort, or any other aspect of the imaging process, along with any combination of the foregoing that is known or becomes known in the art.

It should also be noted that FIG. 4B is a cutaway view of the breast stabilizer unit of FIG. 4A, and that in light of FIG. 4A, and in some embodiments of the invention, the body portion 404 forms an integrated whole having a permanently continuous internal surface region 408. Continuous internal surface region 408 forms, in some embodiments of the invention, a single circumferential surface region laterally encircling a respective portion of the breast to be imaged. In still further embodiments, the continuous lateral internal surface region forms a single circumferential surface encircling a respective continuous lateral surface portion of the breast and, in addition, including a concave surface region enclosing the entire breast below the upper circumferential surface region 410. That is, in some embodiments, the entirety of the internal surface region 408 forms a single continuous generally concave (but not necessarily monotonic or locally concave) surface region, coterminous at the upper circumferential surface region 410, and bounding a recess (or bore or cavity; see the description of element 428 below) within which the subject breast is disposed for imaging.

Moreover, it should be appreciated that, while in the illustrated embodiment 400 the circumferential region 410 is shown as substantially lying within a single plane, one of skill in the art will appreciate that circumferential region 410 may occupy any curve in three space. Accordingly, any of the above-listed exemplary shapes and curves (and other shapes and curves reasonably suggested by the same to one of skill in the art) will have corresponding three-dimensional counterparts in corresponding embodiments of the invention.

One of skill in the art will appreciate that, in certain embodiments, the particular curve, whether planar or three-dimensional, will be particularly beneficial where it conforms to a corresponding region of the breast being imaged, or of an adjacent region of a patient's chest wall, or both.

In addition, it will be observed that, in respective embodiments of the invention, and in no way one exclusive of the other, circumferential region 410 may include a relatively distinct circular edge, or a smooth curve in three dimensions between external surface region 406 and internal surface region 408. Thus, for example, region 412, shown in FIG. 4B shows a relatively smooth curve at the junction between external surface region 406 an internal surface region 408, whereas region 416 of the same figure, includes a relatively sharp or distinct edge 418.

It also should be noted that any particular article prepared within the scope of the present invention may include one or more of these features in any combination effective to improve the speed or clarity or any other result of the imaging process, as well as the comfort of the user, or any other aspect of the invention.

Also illustrated in breast stabilizer unit 400 is a lower circumferential region 420. As with upper circumferential region 410, lower circumferential region 420 is shown as generally circular in form. Moreover, as illustrated, a circle characterizing the upper circumferential region and a further circle characterizing the lower circumferential region are disposed in generally parallel spaced relation to one another, concentrically about a longitudinal axis 422 of the breast stabilizer unit 400.

However, it should be understood that the lower circumferential region can assume any of the shapes or characteristics of the upper circumferential region discussed above in relation to upper circumferential region 410. Moreover, to the extent that the upper and lower circumferential regions define curves in two or more dimensions, it will be appreciated that those curves may be parallel, as between the upper and lower regions, or may be in any orientation appropriate to the needs of a particular design or embodiment.

It should further be noted that the upper circumferential region 410 defines an upper aperture 424 and the lower circumferential region 420 defines a lower aperture 426 of the breast stabilizer unit 400. Accordingly inner surface region 408, in its broadest extent, defines an internal bore or cavity 428 about longitudinal axis 422. It will be appreciated, however, that in certain embodiments of the invention, internal surface region 408 will be continuous below aperture 424, and accordingly the lower aperture 426 of the breast stabilizer 400 will be closed. Correspondingly, the internal cavity 428 will form a recess, closed at its lower end, and having a lower surface region contiguous with the balance of, and forming a portion of, internal surface region 408.

One of skill in the art will appreciate that this lower surface region will have any form appropriate to improving the imaging function or comfort of the patient provided by the breast stabilization unit 400.

It will be apparent from the illustration that the exemplary outer 406 and inner 408 surface regions define a cross-section 430 having generally arcuate outer 432 and inner portions 434. It should be appreciated, however, that these curves are merely exemplary of a wide variety of geometric forms, linear, arcuate, and any combination thereof, that serve the purposes of the invention in a particular application. Moreover, the particular curvature, planarity, texture, or other characteristic of any localized region of outer surface region 406 or inner surface region 408 will, in certain embodiments, vary from place to place about the respective surface region.

Accordingly, in certain aspects or embodiments of the invention, the breast stabilizer unit 400 will include apertures, through-holes, and/or other features about any of surface region 406 and 408 considered to be beneficial by the designer of a particular embodiment of the invention. Moreover, in certain embodiments of the invention, the region between surface regions 406 and 408 will include features and characteristics such as localized apertures, porosity, embedded elements for structural or indicative purposes, or any other characteristic that assists in promoting the functionality, comfort or aesthetics of a particular breast stabilizer unit embodiment.

It will be appreciated by one of skill in the art that, in many embodiments, one or more materials will be selected and included within the breast stabilizer unit 400 that serve to improve its function. Thus, in certain embodiments, the breast stabilizer unit 400 will include a material that is relatively transparent to x-ray radiation. In other embodiments of the invention, relatively x-ray-opaque materials will be employed within all or a portion of the breast stabilizer unit 400. Such materials will serve, in respective embodiments, to provide datum or registration points for localization of a particular region of the physical breast with respect to a corresponding region of an image or data set formed during CBBCT imaging.

It will also be appreciated that, in certain embodiments and depending on the material or materials of the breast stabilizer unit, a hole, recess, or aperture in the material of the breast stabilizer unit will be visible in a subsequent CBBCT image. Accordingly, the placement of appropriate holes, recesses and apertures about the breast stabilizer unit can also be used to localize a particular region of the physical breast to a corresponding region of an image or data set.

In other embodiments, one or more layers of material such as, for example, a metallic or other material, may be deposited within the bulk of the cross-section 430, or in a surface layer on one or both of external surface region 406 an internal surface region 408. Such a metallic material or other material will be selected to assist in filtering and/or spectrum shaping of the impinging x-rays in a manner that benefits a particular imaging process. Accordingly, in certain embodiments of the invention, the breast stabilizer unit 400 will include a metallic material adapted to produce a relatively narrow x-ray spectrum traversing the breast consistent with the application of, for example, phase contrast CBBCT.

In certain embodiments of the invention, the thickness of a surface layer will vary from region to region about the breast stabilizer unit in a manner that allows filtering and/or intensity control of the x-rays reaching the breast. In still further embodiments, a material within the bulk or on the surface of the breast stabilizer unit 400 will include a localized aperture for a region of particular interest and/or radiation (e.g., x-ray) shielding for a region of the breast where imaging is not required.

The reader will appreciate that, in particular aspects and embodiments of the invention, specific materials will be selected for inclusion within, or adjacent to, internal surface region 408. Such materials will be chosen to promote the comfort and/or well-being of the patient where patient skin contacts the surface region. Thus, in certain embodiments, materials having a beneficially low durometer will be selected. In some embodiments, a material will be selected having a wicking characteristic adapted to avoid an accumulation of perspiration. Accordingly, in certain embodiments, woven and/or non-woven textiles will be selected for inclusion within or adjacent to internal surface region 408. Of course, materials having advantageous biocompatibility characteristics will be desirable in many embodiments. It should be understood that these are merely exemplary of a variety of characteristics that will become apparent in light of the totality of the present disclosure.

In light of the foregoing, it will be appreciated that use of any of the following materials will be considered to be desirable in a particular embodiment of the invention.

Suitable polymers such as polyethylene, polypropylene, polybutylene, polystyrene, polyester, acrylic polymers, polyvinylchloride, polyamide, or polyetherimide like ULTEM®; a polymeric alloy such as Xenoy® resin, which is a composite of polycarbonate and polybutyleneterephthalate or Lexan® plastic, which is a copolymer of polycarbonate and isophthalate terephthalate resorcinol resin (all available from GE Plastics), liquid crystal polymers, such as an aromatic polyester or an aromatic polyester amide containing, as a constituent, at least one compound selected from the group consisting of an aromatic hydroxycarboxylic acid (such as hydroxybenzoate (rigid monomer), hydroxynaphthoate (flexible monomer), an aromatic hydroxyamine and an aromatic diamine, polyesterimide anhydrides with terminal anhydride group or lateral anhydrides or combinations thereof.

In addition, any polymeric composite such as engineering prepregs or composites, which are polymers filled with pigments, carbon particles, silica, glass fibers, conductive particles such as metal particles or conductive polymers, or mixtures thereof may also be used. For example, a blend of polycarbonate and ABS (Acrylonitrile Butadiene Styrene) may be used.

Where surface films or bulk inclusions are desired, it will be appropriate to include one or more metal or metallic alloys such as, for example, stainless steel; aluminum; an alloy such as Ni/Ti alloy; and any of the amorphous metals.

In addition, natural polymers and natural materials will be included in certain embodiments including, by way of example, felted or woven textiles including one or more of, for example, cotton, bamboo, linen, wool, leather, cork and other arboreal products, papers, and clays. It will be appreciated that these materials may be employed alone or that one or more of these materials will be employed in any combination and in any spatial arrangement including in layers, particulate form, slurries, gels or other physical forms.

Additional features of a breast stabilizer unit 400 will be described below in relation to further embodiments and, particularly, in relation to coupling features (e.g., 208, 210) as addressed briefly above in the context of FIG. 2.

Figure 5:
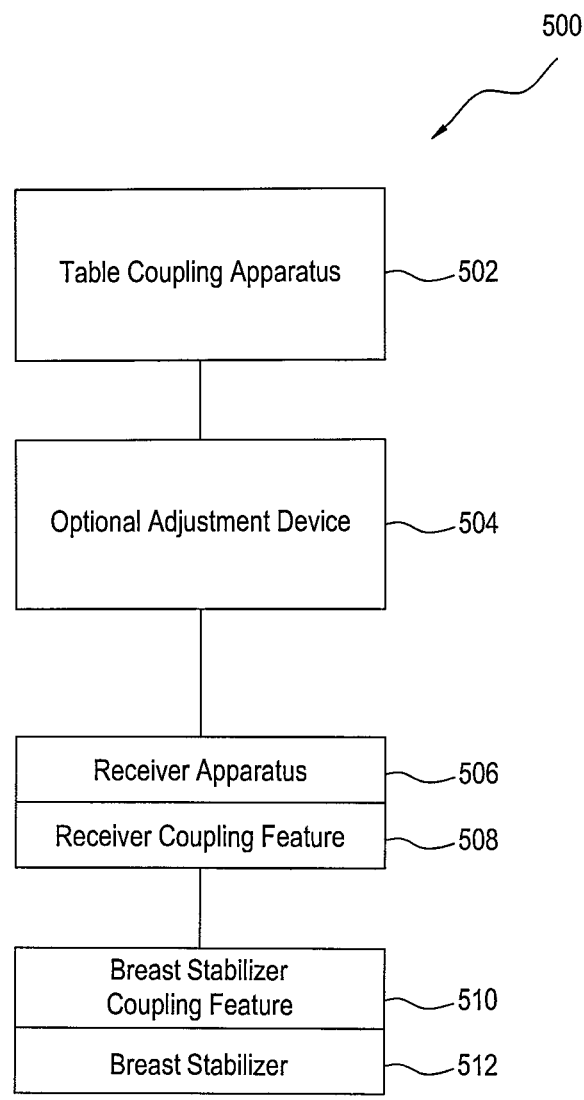
FIG. 5 shows in block diagram form the structural relationship of certain aspects of an exemplary CBBCT breast imaging system prepared according to principles of the invention.

FIG. 5 shows, in block diagram form, a portion of a further example of a subsystem 500 for breast support and fixturing prepared according to principles of the invention. Unlike system 200, described above, subsystem 500 is supported by a table or patient interface panel (exemplified as element 120 of FIG. 1) of the breast imaging system. As will be further discussed below, in certain embodiments of the invention, a table coupling apparatus 502 is operatively coupled to an upper or lower surface region of the patient table portion, or therebetween. Accordingly, during operation, a patient is disposed prone on an upper surface region (e.g., 122) of the patient table, and the subject breast is disposed through an aperture of the table portion so as to interface with the subsystem 500. In certain embodiments of the invention, the table coupling portion is integrally formed as a part of the patient table.

In certain embodiments of the invention, the table coupling apparatus 502 is coupled to an adjustment device 504. Adjustment device 504 is arranged and configured to allow for adjustment of the spatial location of a subject breast with respect, for example, to the imaging apparatus of a breast imaging system. Accordingly, in certain embodiments, adjustment device 504 is adapted to adjust an elevation of a portion of the breast with respect to the patient table and, hence, with respect to an imaging region of the above-referenced imaging apparatus.

As illustrated, a receiver apparatus 506 is operatively coupled to the adjustment device. The receiver apparatus 506 includes a body portion and/or a support member. In certain embodiments, the receiver apparatus 506 includes a receiver coupling feature 508. The receiver coupling feature 508 includes at least one surface region that is operatively complementary to a corresponding surface region of a coupling feature 510 of a breast stabilizer unit 512.

As will be further discussed below, the breast stabilizer unit 512 is configured to support the breast of a patient in a manner that positions and stabilizes the breast for imaging. Accordingly, in certain embodiments of the invention, the breast stabilizer unit 512 will include an interface surface region. When in use, a surface region of the patient's breast is supported, directly or indirectly, on the interface surface region.

It should be noted that, in certain embodiments, the adjustment device 504 is omitted and the receiver apparatus 506 is coupled directly to the coupling apparatus 502. In such an arrangement, where adjustment of the position of the breast is desirable, the size or other configuration of the breast stabilizer unit 512 may be selected to provide the desired breast location (in the manner described above). Accordingly, in certain embodiments of the invention, the adjustment device 504 described above may be omitted, and other arrangements made to provide for a desirable positioning of the breast with respect to an imaging apparatus.

Figure 6:
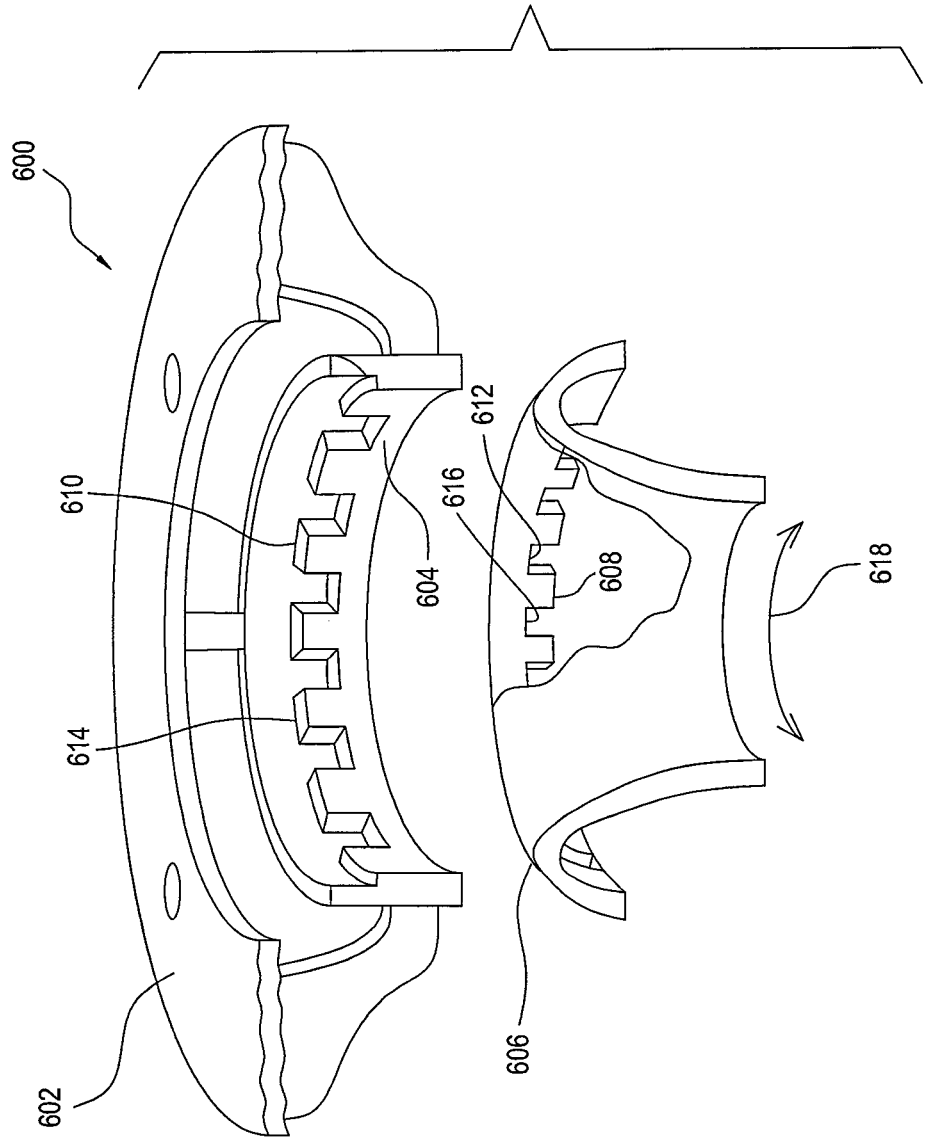
FIG. 6 shows in schematic cutaway perspective view, certain aspects of an exemplary CBBCT breast imaging system including portions of a coupling feature of a breast stabilizer unit prepared according to principles of the invention.

In light of the foregoing disclosure, FIG. 6 shows, in cutaway schematic perspective view, a portion 600 of a breast imaging system including certain aspects of an interface between a receiver apparatus and a breast stabilizer unit. Specifically, FIG. 6 shows a portion of receiver apparatus 602 including a receiver coupling feature 604, and a breast stabilizer unit 606 including a corresponding breast stabilizer unit coupling feature 608.

In the exemplary apparatus of FIG. 6, the receiver coupling feature 604 and breast stabilizer coupling feature 608 include complementary crenellated surface regions 610, 612 respectively. One of skill in the art will readily appreciate that the generally rectangular projections, e.g. 614 of the receiver coupling feature 604 will be sized and configured to be received snugly within the corresponding generally rectangular recesses 616 of the breast stabilizer unit coupling feature 608, and vice versa.

Moreover, it will be apparent to one of skill in the art that where, in certain embodiments, the sizing of the various crenellations are generally uniform, a wide variety of symmetric placements of the breast stabilizer unit with respect to the receiver will be possible. Thus, a rotational adjustment of the breast stabilizer unit about a longitudinal axis of the receiver unit (and thus, in certain embodiments, about an axis of rotation 108 of the gantry 104) will be facilitated.

This will be of particular value in an embodiment where an asymmetric characteristic of the breast stabilization unit is chosen to conform to a corresponding asymmetry of the patient's breast. Thus, the breast support unit can be rotated 618 until it is properly aligned with the patient's breast as the patient lies prone on the patient support table.

Figure 7:
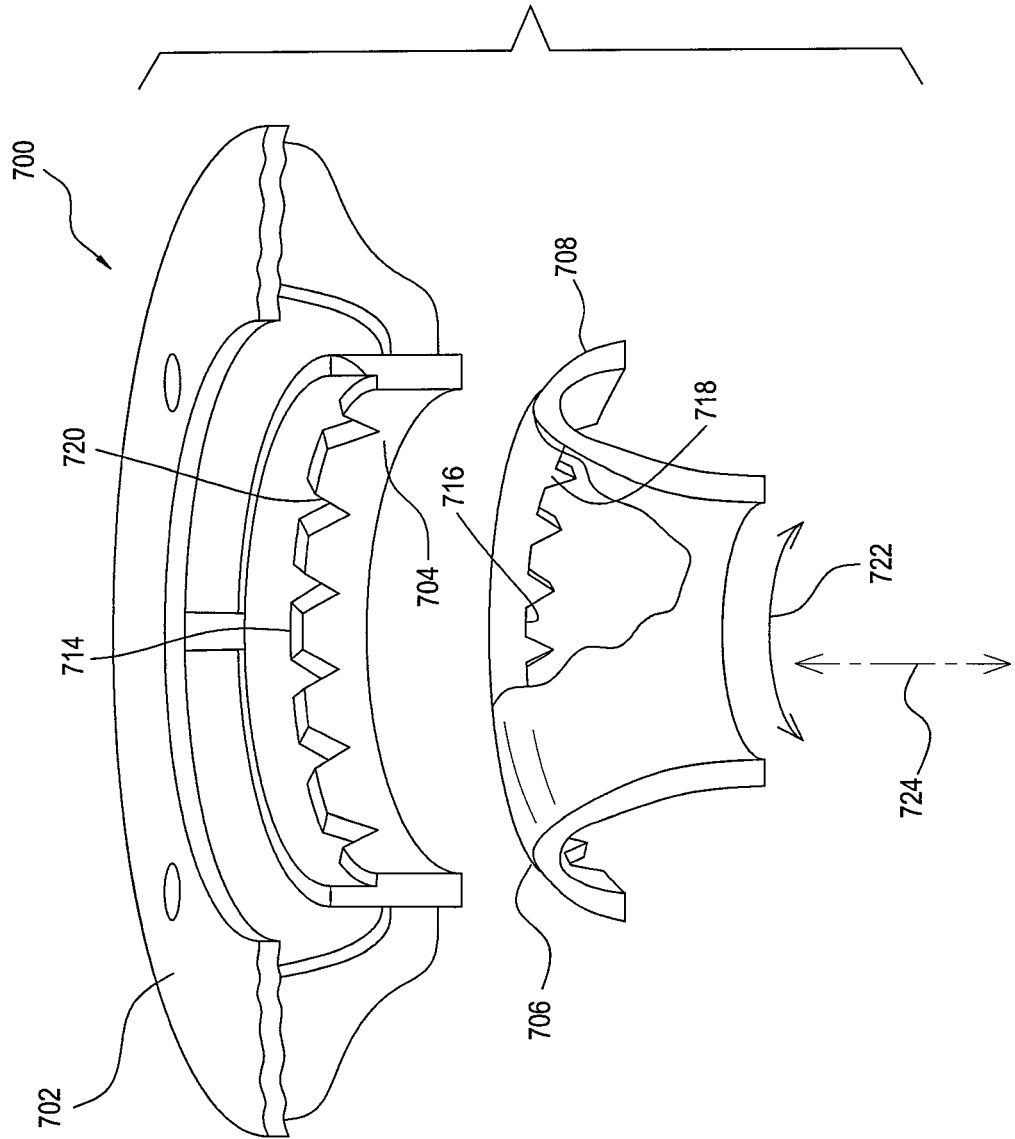
FIG. 7 shows in schematic cutaway perspective view, further aspects of an exemplary CBBCT breast imaging system including portions of a coupling feature of a breast stabilizer unit prepared according to principles of the invention.

FIG. 7 shows, in cutaway schematic perspective view, a portion 700 of a breast imaging system including certain aspects of an interface between a receiver apparatus and a breast stabilizer unit. Specifically, FIG. 7 shows a portion of a further receiver apparatus 702 including a receiver coupling feature 704, and a breast stabilizer unit 706 including a corresponding breast stabilizer unit coupling feature 708.

In the exemplary apparatus of FIG. 7, the receiver coupling feature 704 and breast stabilizer coupling feature 708 include complementary generally triangular and truncated triangular features. In view of the discussion above in relation to FIG. 6, one of skill in the art will readily appreciate that the generally truncated triangular projections, e.g. 714 of the receiver coupling feature 704 will be sized and configured to be received snugly within the corresponding generally truncated triangular recesses 716 of the breast stabilizer unit coupling feature 708. Correspondingly, the generally triangular projections 718 of the breast stabilizer coupling feature 708 will be received within the generally triangular recesses 720 of the receiver coupling feature 704.

As in the case of portion 600, the multiplicity of interdigitated projections and recesses allows for adjustment 722 of the breast stabilizer unit 706 about a longitudinal axis 724 so as to conform to imaging requirements, patient comfort, or any other desirable attribute of the system.

It will be apparent to one of skill in the art that the particular configurations of the coupling feature described above are merely exemplary of a wide variety of geometries, including polygonal, arcuate, and any other geometry (see, e.g., the geometries listed above in other contexts).

Figure 8:
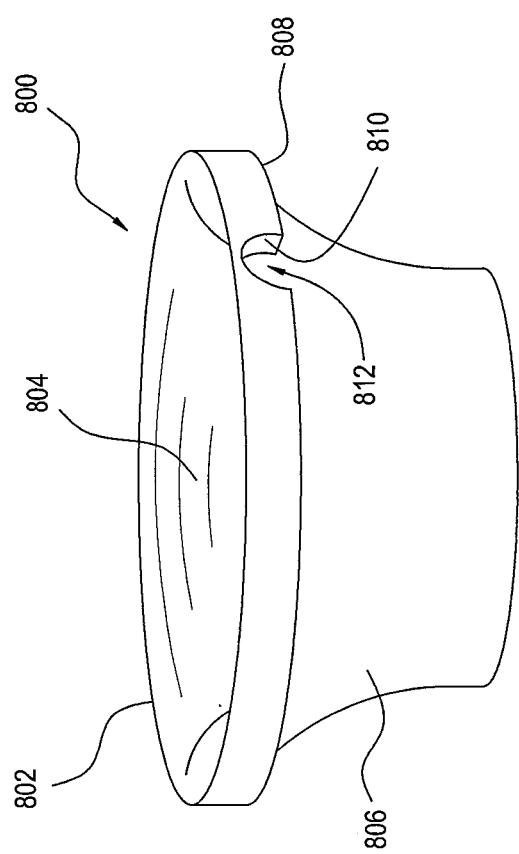
FIG. 8 shows in schematic perspective view, still further aspects of an exemplary CBBCT breast imaging system including portions of a coupling feature of a breast stabilizer unit prepared according to principles of the invention.

Moreover, in certain applications of the invention, a breast stabilization unit will include a coupling feature with a fixed or otherwise variable rotational interface. Thus, FIG. 8 shows, in schematic perspective view, another exemplary arrangement of a breast stabilization unit 800 prepared according to principles of the invention.

Breast stabilization unit 800 includes a body portion 802. The body portion 802 has an internal surface region 804 and an external surface region 806. In the illustrated embodiment, the internal surface region 804 and external surface region 806 meet at a generally circular upper circumferential region 808.

In the illustrated example, the breast stabilization unit 800 includes a coupling feature in the form of a surface region 810 defining a recess or keyway 812 disposed in proximity to the generally circular upper circumferential region 808. In light of the foregoing disclosure, one of skill in the art will appreciate that the recess or keyway 812 is adapted to receive a corresponding projection or key of a receiver portion. It will be understood that the geometry of the key will be complementary to that of the keyway 812 in most cases (although not in every embodiment).

Figure 9:
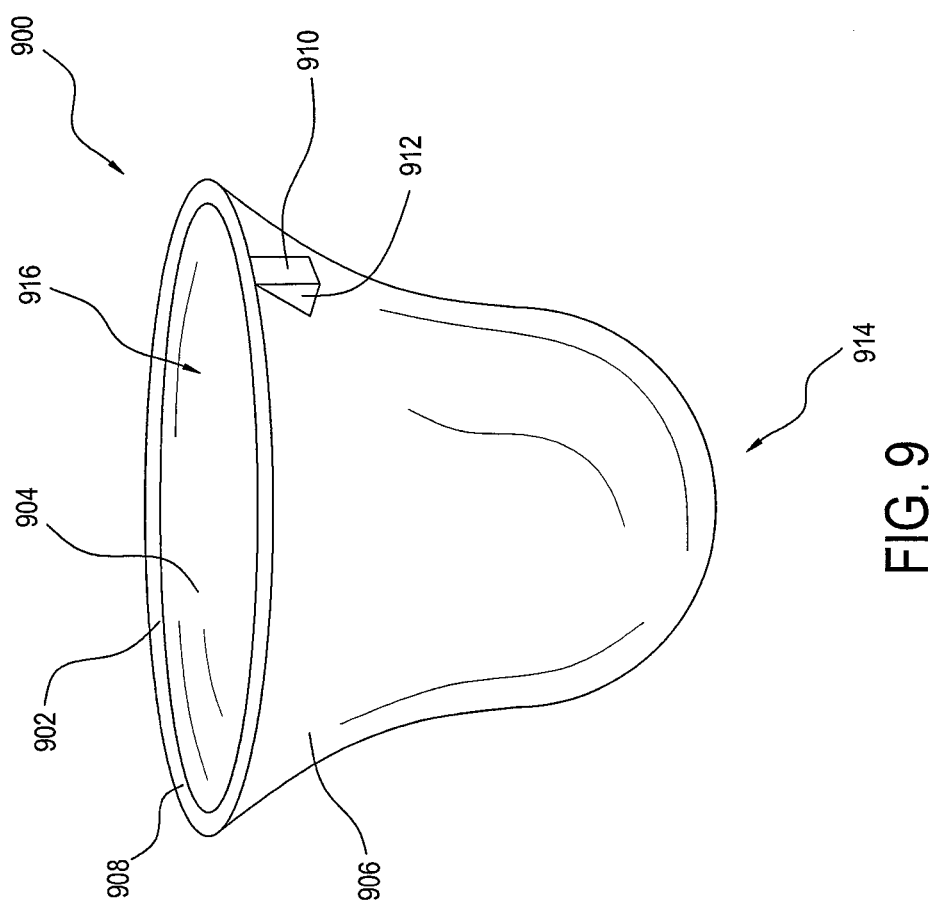
FIG. 9 shows in schematic perspective view, yet further aspects of an exemplary CBBCT breast imaging system including portions of a coupling feature of a breast stabilizer unit prepared according to principles of the invention.

FIG. 9 shows, in schematic perspective view, yet another exemplary arrangement of a breast stabilization unit 900 prepared according to principles of the invention.

Breast stabilization unit 900 includes a body portion 902. The body portion 902 has an internal surface region 904 and an external surface region 906. In the illustrated embodiment, the internal surface region 904 and external surface region 906 meet at a generally circular upper circumferential region 908.

In the illustrated example, the breast stabilization unit 900 includes a coupling feature in the form of a surface region 910 defining a projection or key 912 disposed in proximity to the generally circular upper circumferential region 908. In light of the foregoing disclosure, one of skill in the art will appreciate that the projection or key 912 is adapted to be received in a corresponding recess or keyway of a receiver portion so as to form mutually interlocking elements. It will be understood that the geometry of the keyway will be complementary to that of the key 912 in most cases (although not in every embodiment).

It will also be noted that breast stabilization unit 900 exemplifies one of many possible arrangements and configurations in which a lower end 914 of the breast stabilization unit is closed. Accordingly, recess 916 of the breast stabilization unit 900 is adapted to receive and fully contain the breast being imaged. Among other advantages, this configuration allows the breast stabilization unit 900 to serve a dual purpose as a safety enclosure for the breast, so as to avoid any possibility of the breast mechanically interfering with the rotating imaging apparatus (i.e., the x-ray source, the x-ray detector, the rotating gantry, etc.).

Moreover, it will be appreciated that a fully enclosed breast stabilization unit, as exemplified by breast stabilization unit 900, serves to confine the breast within a uniform spatial envelope. This will be understood to have particular benefits in various imaging operations, and other procedures, associated with an imaging system according to the present invention (for example, as with a bow tie filter, where the uniform symmetrical shape of the supported breast will match the contours of the bow tie filter).

Figure 10:
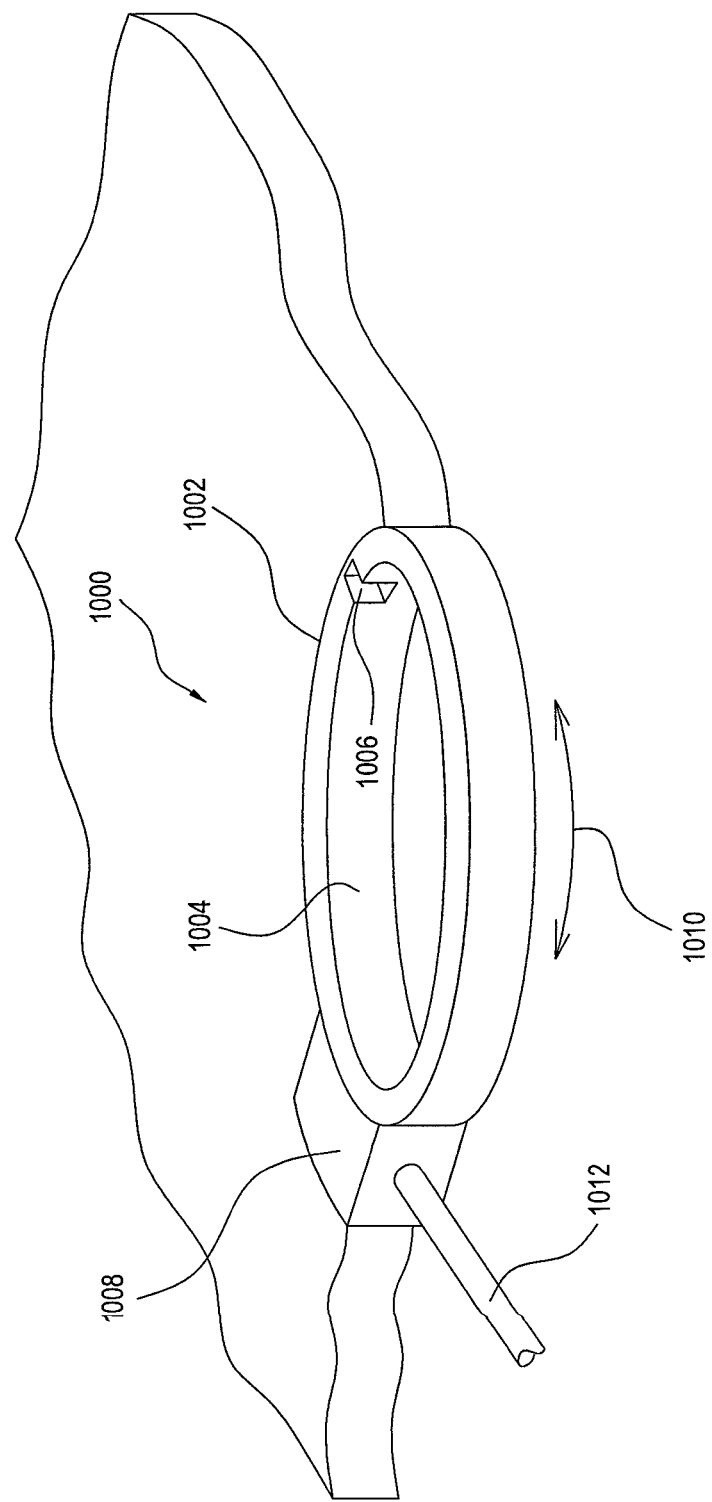
FIG. 10 shows in schematic cutaway perspective view, certain aspects of an exemplary CBBCT breast imaging system including portions of a receiver and coupling feature for receiving a breast stabilizer unit prepared according to principles of the invention.

FIG. 10 shows, in schematic perspective cutaway view, a further exemplary arrangement of a receiver apparatus 1000 prepared according to principles of the invention. Receiver apparatus 1000 includes a receiver body member 1002. In the illustrated embodiment, the receiver apparatus body member 1002 has a generally toroidal form. While the illustrated toroid has a generally rectangular cross-section, one of skill in the art will appreciate that this is merely exemplary and that any of a wide variety of cross-sections will be employed according to the needs of a particular application.

In the exemplary embodiment presented, the receiver body 1002 includes a coupling feature including an internal generally circumferential engagement surface 1004, and a keyway 1006.

It will be appreciated by one of skill in the art that the keyway is optional, inasmuch as certain embodiments of the invention will include a breast stabilizer having neither key nor keyway, but which is held in place by friction between the circumferential engagement surface 1004 and a corresponding engagement surface of the breast stabilizer. In other embodiments and applications of apparatus prepared according to the invention, it will be considered desirable to allow the breast stabilizer to rotate more or less freely, rather than being maintained in a relatively fixed relationship to the patient table.

In the illustrated embodiment, the receiver apparatus 1000 is adapted to receive, for example, a breast stabilizer unit like unit 900 shown in FIG. 9. Accordingly, key 912 is adapted to be received in keyway 1006.

In certain embodiments, as shown, receiver 1000 includes an actuator 1008. Actuator 1008 includes an engagement mechanism that engages a corresponding element of receiver body 1002. In operation, before or after the coupling feature of the breast stabilizer unit is engaged with the coupling feature of receiver 1000, a rotary position of the receiver body 1002 can be adjusted 1010 as desired for patient comfort and according to any other requirement associated with using the imaging system. In the exemplary embodiment illustrated, this rotation is motivated by manual rotation of a driveshaft 1012 of the actuator 1008. The driveshaft will, for example, be coupled to a worm gear that engages a corresponding rack of the receiver 1000. One of skill in the art will readily appreciate, however, that a wide variety of other actuators, both manually and automatically activated, will be employed in respective embodiments of the invention.

Figures 11A, 11B:
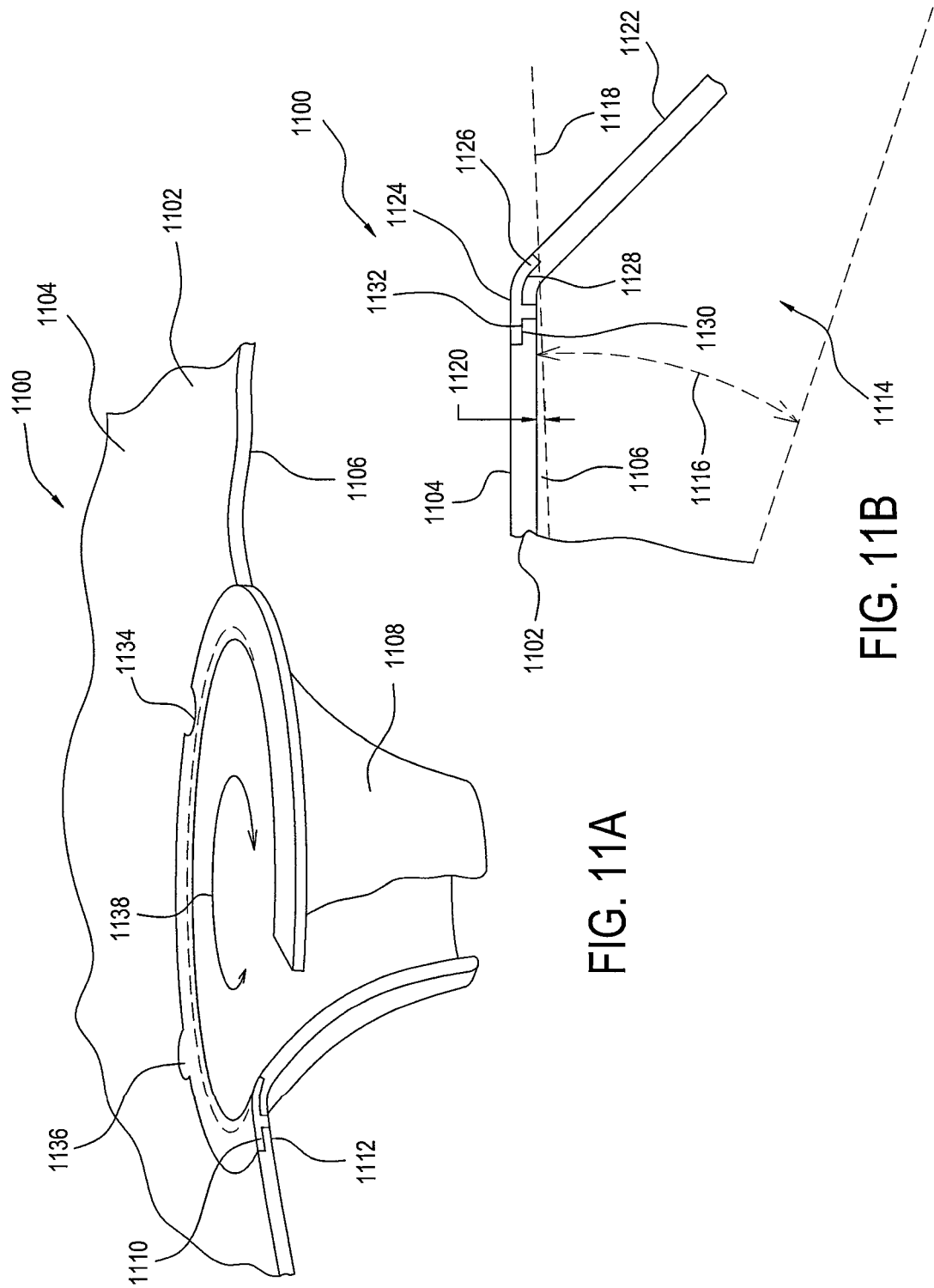
FIG. 11A shows in schematic cutaway perspective view, certain aspects of an exemplary CBBCT breast imaging system including certain aspects of an exemplary breast stabilizer unit prepared according to principles of the invention.
FIG. 11B shows in schematic cross-sectional detail elevation, additional aspects of an exemplary CBBCT breast imaging system including certain aspects of an exemplary breast stabilizer unit prepared according to principles of the invention.

FIG. 11A shows, in schematic perspective cutaway view, further aspects and characteristics of an exemplary imaging system 1100 prepared according to principles of the invention. As illustrated, the imaging system includes a patient table 1102 with an upper surface 1104 and a lower surface 1106. Imaging system 1100 presents certain particularly desirable features including a breast stabilization unit 1108 that is prepared and configured to allow imaging of substantially the entire subject breast and, in some cases, a portion of the corresponding chest wall.

Rather than having a discrete receiver, the illustrated embodiment shows a surface region 1110 of the patient table 1102 that serves as a receiver coupling region 1112.

Referring now to FIG. 11B in conjunction with FIG. 11A; FIG. 11B shows in schematic cross-sectional view, further detail of the exemplary imaging system 1100. As noted above, patient table 1102 includes an upper surface region 1104 and a lower surface region 1106.

When in operation, an x-ray beam 1114 fills a spatial region below surface 1106 and spans 1116 a cross-sectional area designed and configured to illuminate a target region of the subject breast, up to and including the entire breast.

It should be understood that, in certain applications of the imaging system 1100, it is desirable for an upper boundary 1118 of the x-ray beam 1114 to be disposed as close as possible to lower surface 1106 of patient table 1102 (i.e., minimizing or optimizing distance 1120), so as to permit imaging of the breast as near as possible or practical to the patient's chest wall. Indeed, in certain embodiments of the invention, it will be possible to image a portion of the chest wall with the imaging system 1100.

In the illustrated embodiment, the breast stabilization unit 1108 includes a first body element 1122 and a second rim element 1124. The first body element 1122 will include, in certain embodiments, a structural material having mechanical characteristics sufficient to support a patient breast and a material that is relatively x-ray transparent. In certain embodiments of the invention, a single material will embody both of these characteristics.

In certain embodiments of the invention, the first body element 1122 will be substantially fixedly coupled to the second rim element 1124 at respective interface surface regions 1126, 1128. In respective embodiments this coupling will be achieved through the use of a chemical adhesive, a physical bond, a mechanical fastener, mechanical swaging, a weld, such as a thermal weld, an ultrasonic weld, a laser weld, or a chemical weld, or any other coupling mechanism appropriate to the requirements of the application, including any combination thereof.

In the illustrated example the second rim element 1124 includes a rim coupling surface region 1130. The rim coupling surface region 1130, is adapted and configured to interface with a complementary patient table coupling surface region 1132, to form a secure coupling between the patient table 1102 and the breast stabilization unit 1108.

As per the illustrated example, the characteristics of the materials selected, and the configuration of those materials allow the patient table 1102 to support the breast stabilization unit 1108 without substantially interfering with the upper boundary 1118 of the x-ray beam 1114. The materials of the second rim element 1124 will thus be selected accordingly and will, in respective embodiments, include any of a metallic material, a synthetic polymer material, a glass material, a natural polymer material, or any other structural material appropriate to the requirements of a particular embodiment, including combinations thereof.

In the illustrated example, the second rim element 1124 is keyed 1134, 1136 to the patient table 1102 to limit rotation 1138 of the breast stabilization unit 1108 about a longitudinal axis thereof. As has been discussed above, however, in other embodiments of the invention, the design, materials and configuration of the second rim element 1124 and the corresponding coupling surface region 1132 of the patient table 1102 will be selected and configured to allow frictional rotation, or substantially free rotation of the breast stabilization unit 1108.

It will also be appreciated that the second rim element 1124 will, in respective embodiments, have respective radial dimensions such that a single aperture of substantially fixed dimension through patient table 1102 will accommodate a wide variety of breast stabilization elements e.g., 1108 having different respective diameters and other configurations and parameters, where the corresponding radial width of the second rim element 1124 serves to adapt these different dimensions to one another.

One of skill in the art will appreciate that the presence of a discrete rim element is optional, and that in certain embodiments of the invention, a single uniform material will constitute both the first body portion 1122 of the breast stabilization unit 1108 and the second rim element 1124 of the breast stabilization unit 1108 as a single integrally formed item. In still other embodiments of the invention, internal reinforcement, such as, for example, reinforcing fibers of glass, carbon, polymer, or other material, will be present in one or another region of the breast stabilization unit 1108. It will be appreciated that any transition in composition between one and another of such regions may be abrupt or gradual as deemed appropriate in relation to the requirements of a particular mode or application of the invention.

Finally, it will be understood in light of the entirety of the present disclosure that having established illustrated exemplary characteristics of the aperture and interface surface region 1132 of the patient table 1102, these characteristics will form a standard interface to which any of a wide variety of breast stabilization units will be prepared and coupled. Accordingly, in certain embodiments of the invention, a breast stabilization unit will be prepared having the standard interface at its upper radial periphery, and having bespoke dimensions customized according to the requirements and/or parameters (e.g., dimensions) of a particular patient, procedure, diagnostic or mode of operation. In certain embodiments, as discussed above, the breast stabilization unit will be prepared using locally available (i.e., at the imaging facility) additive or subtractive manufacturing equipment and processes.

Figure 12:
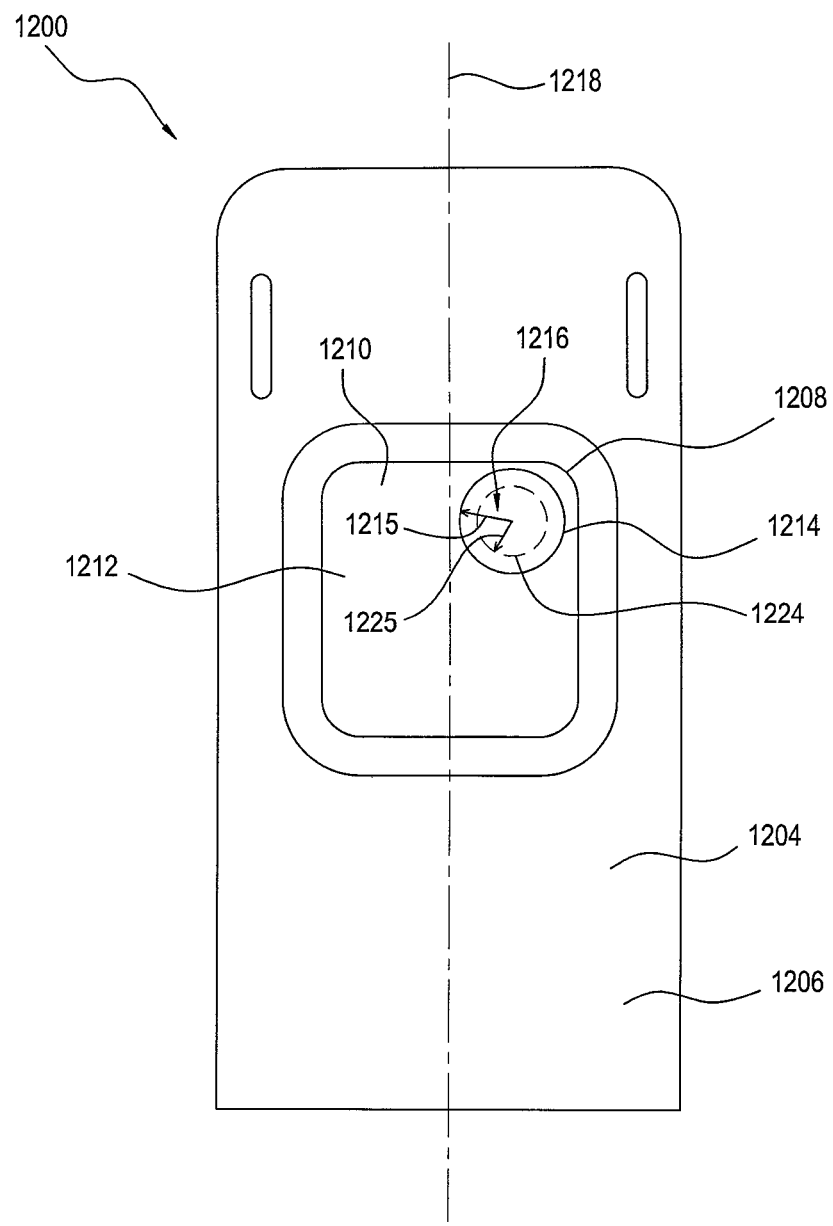
FIG. 12 shows, in schematic top view, certain features of an exemplary CBBCT imaging system, including a patient interface panel, prepared according to principles of the invention.

FIG. 12 shows, in schematic top view, certain aspects of an exemplary CBBCT imaging system 1200, including a patient interface panel (or patient table) 1204.

The patient interface panel 1204 includes a patient interface surface region 1206 adapted to support a patient during scanning. In various embodiments of the invention, the patient interface surface region 1206 includes an inner circumferential edge 1208 defining an aperture of the patient interface surface region through the patient interface panel. In some embodiments of the invention, the aperture is adapted to receive a breast of the patient disposed therethrough. In other embodiments, including that illustrated in FIG. 12, the aperture is adapted to receive a patient interface subpanel 1210 that traverses circumferential edge 1208. The patient interface subpanel 1210 is coupled to and/or supported by the patient table 1204.

In considering inner circumferential edges, it will be apparent that the particular shape of the circumferential edge will be selected in a corresponding embodiment so as to optimize considerations such as functionality and ease of manufacture. Accordingly, the geometry shown is merely exemplary of a wide variety of configurations that will be immediately apparent to one of skill in the art in light of the entirety of the present disclosure.

The patient interface subpanel 1210 includes a subpanel surface region 1212. A further inner circumferential edge 1214 defines a subpanel aperture 1216 through the subpanel. In the configuration illustrated, the subpanel aperture 1216 is disposed to the right of a longitudinal centerline 1218 of the patient interface panel 1204. Accordingly, in typical operation of the CBBCT imaging system, a right breast of the patient will be disposed through the subpanel aperture 1216 during imaging.

One of skill in the art will appreciate that, in certain embodiments of the invention, a plurality of subpanels will be provided that include apertures of different respective dimensions. For example, a subpanel having an internal circumferential edge 1224 defining an aperture with a smaller diameter 1225 (as compared with illustrated aperture diameter 1215 defined by inner circumferential edge 1214) will be available. Accordingly, technical or medical personnel will be able to select and install a subpanel having an aperture appropriate for the size of the breast of the particular patient to be imaged.

In other embodiments of the invention, the adjustment of aperture size will be effected by operation of an adjustment mechanism such as an iris leaf diaphragm aperture mechanism. In certain embodiments the adjustment mechanism will be substantially permanently coupled to the patient table 1204. In other embodiments of the invention, the adjustment mechanism will be coupled to a removable subpanel like subpanel 1210 described above.

In certain embodiments of the invention, the aperture for receiving the breast to be imaged is disposed generally coincident with the centerline of the patient table. In such an embodiment, the patient will be positioned to align the breast to be imaged with the centerline of the table. Consequently, no additional transverse mechanism is required to align the breast with the axis of rotation of the gantry. It will be appreciated by one of skill in the art that this alignment of the breast aperture may be effected by providing the aperture directly in the patient table, or, alternately, in a subpanel configured for attachment or coupling to the patient table.

Figure 13:
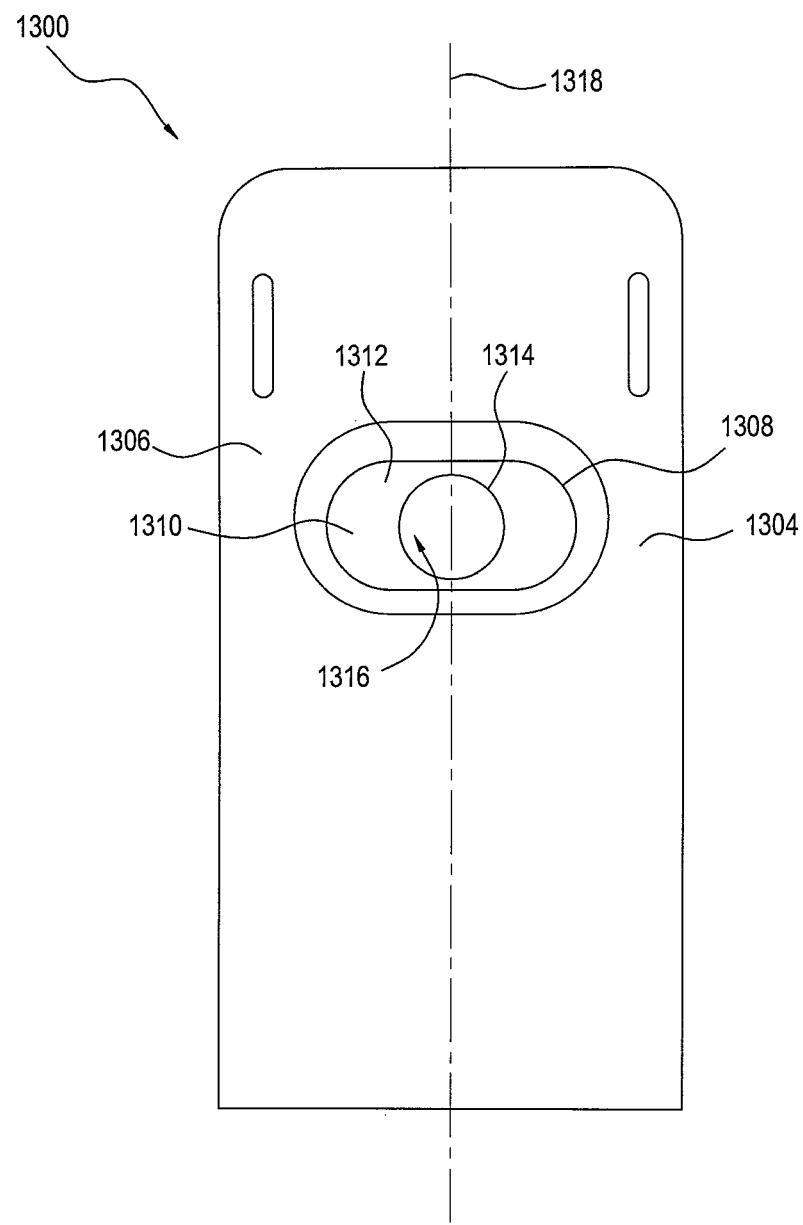
FIG. 13 shows, in schematic top view, additional features of an exemplary CBBCT imaging system, including a patient interface panel, prepared according to principles of the invention.

Accordingly, FIG. 13 shows, in schematic top view, certain aspects of an exemplary CBBCT imaging system 1300 including a patient interface panel (or patient table) 1304.

The patient interface panel 1304 includes a patient support surface region 1306 adapted to support a patient during scanning and a subpanel 1310 that traverses an inner circumferential edge 1308 of the patient support surface region 1306. The subpanel 1310 is coupled to and/or supported by the patient interface panel 1304.

The subpanel 1310 includes a subpanel surface region 1312. A further inner circumferential edge 1314 defines a subpanel aperture 1316 through the subpanel. In the configuration illustrated, the subpanel aperture 1316 is disposed coincident with a longitudinal centerline 1318 of the patient table 1304. Accordingly, in typical operation of the CBBCT imaging system, either breast of the patient may be disposed through the subpanel aperture 1316 during imaging, with the patient being arranged on the patient support surface region 1306 of the patient interface panel 1304 accordingly.

Although the inner circumferential edges 1214, 1224, 1314, illustrated and discussed above are shown with substantially circular aspects, one of skill in the art will appreciate that the circumferential edge may be of any form considered advantageous according to the requirements of a particular application of the invention. Accordingly, in certain embodiments of the invention, the circumferential edge will be generally elliptical, or may be generally triangular, or of any other regular or irregular polygonal form, or of any arcuate form or any combination of arcuate and linear segments, or any combination of the foregoing, all of which are considered to be within the scope of the present disclosure.

Figure 14:
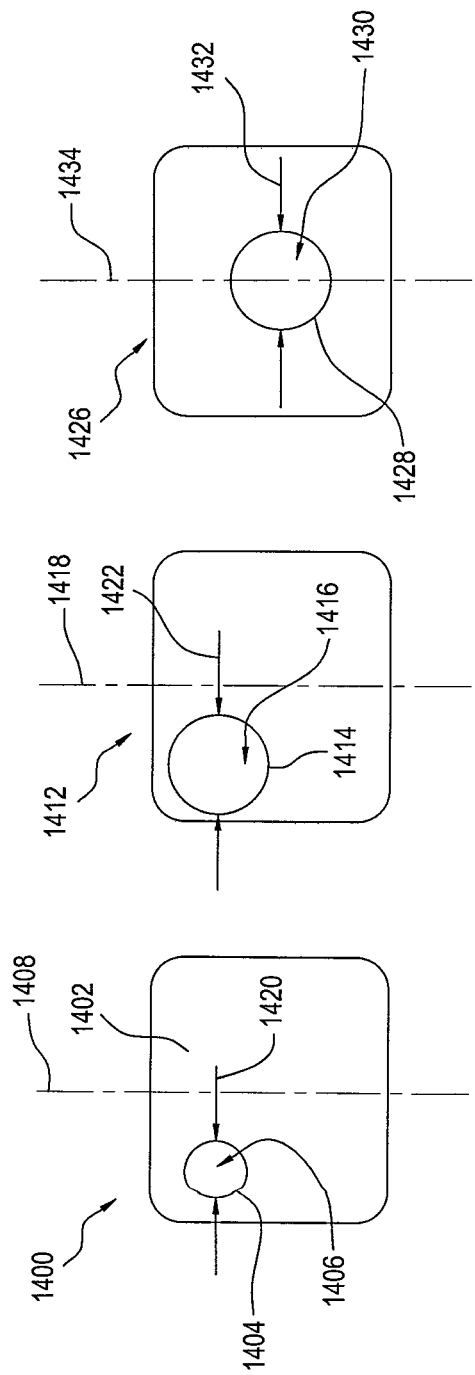
FIG. 14A shows, in schematic top view, certain features of a CBBCT imaging system prepared according to principles of the invention, including exemplary subpanel elements.
FIG. 14B shows, in schematic top view, additional aspects of a CBBCT imaging system prepared according to principles of the invention, including exemplary subpanel elements.
FIG. 14C shows, in schematic top view, further exemplary aspects of a CBBCT imaging system prepared according to principles of the invention, including exemplary subpanel elements.

FIGS. 14A-14C show respectively, in schematic top view, exemplary subpanels having a variety of aperture locations and sizes.

Referring first to FIG. 14A, subpanel 1400 includes a subpanel surface region 1402. An inner circumferential edge 1404 defines a subpanel aperture 1406 through the subpanel. Consistent with the discussion above, the aperture 1406 is adapted to receive a patient breast to be imaged therethrough. In the configuration illustrated, the subpanel aperture 1406 is disposed to the left of a longitudinal centerline 1408 of the subpanel 1400. Accordingly, in typical operation of the CBBCT imaging system, a left breast of the patient will be disposed through the subpanel aperture 1406 during imaging.

FIG. 14B shows a subpanel 1412 similar to subpanel 1400. As with subpanel 1400, subpanel 1412 has an inner circumferential edge 1414 that defines a subpanel aperture 1416 through the subpanel 1412. Like aperture 1406, aperture 1416 is disposed to the left of a longitudinal centerline 1418 of the subpanel 1412. However, aperture 1406 has a diameter of 1420 that is relatively smaller than the corresponding diameter 1422 of aperture 1416.

FIG. 14C shows a subpanel 1426 similar to subpanels 1400 and 1412. As with subpanel 1400, subpanel 1426 has an inner circumferential edge 1428 that defines a subpanel aperture 1430 through the subpanel 1426. Aperture 1430 has a diameter of 1432 that is substantially equal to corresponding diameter 1422 of aperture 1416. However, a centroid of aperture 1430 is disposed substantially coincident with centerline 1434 of the subpanel 1426. Accordingly, whereas apertures 1406 and 1416 are primarily configured for receiving a left breast of the patient for imaging, aperture 1430 is well adapted to receiving either a left breast or a right breast.

It will also be appreciated by one of skill in the art that, where appropriate perimeter configurations and coupling features are provided, symmetries of the illustrated panels will be used in respective embodiments of the invention to image, for example, either a left breast or a right breast by symmetric rotation of subpanel 1400 or 1412 about centerlines 1408 and 1418 respectively, or by a rotation (e.g., of 180° in the plane of the panel) about a centroid of the panel. That is, rotation of the panels about an axis transverse to the centerlines can be used to locate the illustrated apertures relatively higher or lower respectively, according to the needs of a taller or shorter patient.

In light of the foregoing discussion, it will be appreciated by the reader that, in certain embodiments of the invention, a plurality of subpanels will be provided along with an imaging system, such that the subpanel with the appropriate aperture will be selected according to the height, weight, breast size and any other parameter of the patient.

In another aspect or embodiment of the invention, individual reusable subpanels will be purchased so as to be available where required. In still other embodiments of the invention, disposable subpanels will be employed for single use with respective patients, and thereafter discarded.

In another aspect or embodiment of the invention, a disposable liner of, for example, a woven or felted textile material or a polymer sheet, will be provided to accompany a reusable subpanel.

Figure 15:
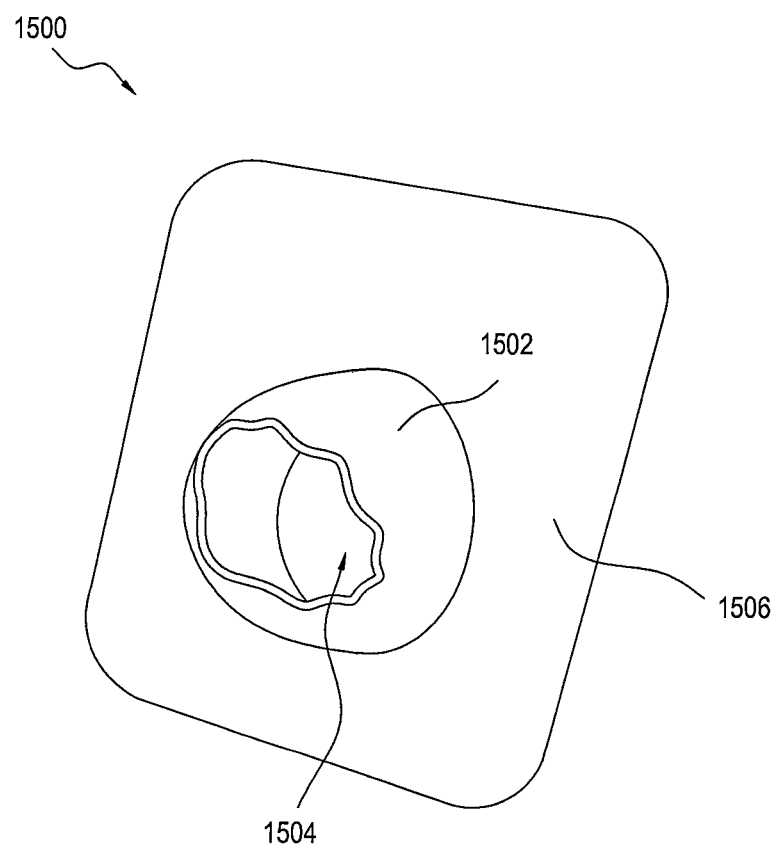
FIG. 15 shows, in distal schematic perspective view, certain further features of a CBBCT imaging system prepared according to principles of the invention, including exemplary breast stabilization features.

In a still further aspect of the invention FIG. 15 shows, in schematic distal cutaway perspective view, a subpanel 1500 including a breast stabilizer unit 1502 adapted and configured to support and stabilize a patient breast during imaging. As illustrated, the breast stabilizer unit 1502 is coupled to the subpanel 1500 at aperture 1504 of distal surface 1506.

In certain applications, the breast stabilizer unit 1502 is configured and adjusted to maintain an approximate geometric centroid of the breast coincident with an axis of rotation of the CBBCT gantry and longitudinal axis 222 of the x-ray beam. It will be appreciated by one of skill in the art, however, that any of a wide variety of placements and configurations of the breast will be desirable in respect to a particular patient, application, or imaging objective, and will be achieved by an appropriate configuration, shape, and placement of the breast stabilizer unit 1502.

In certain embodiments of the invention, the breast stabilizer for a cone beam breast tomographic imaging system includes a body portion, the body portion having an internal surface region and a coupling surface portion, the internal surface region being substantially immobile with respect to the coupling surface portion, the internal surface region includes a breast contact portion, the breast contact portion being adapted to support a corresponding surface region of a patient breast during operation of the cone beam tomographic imaging system, the coupling surface portion being adapted to couple the body portion to a receiver of the cone beam tomographic imaging system.

In certain embodiments of the invention the breast contact portion forms a substantially continuous circumferential surface region of the internal surface region.

In certain embodiments of the invention, the breast stabilizer for a cone beam breast tomographic imaging system has the receiver directly connected to a patient interface panel of the cone beam tomographic imaging system.

In certain embodiments of the invention, the breast stabilizer for a cone beam breast tomographic imaging system has the receiver integrally formed with a patient interface panel of the cone beam tomographic imaging system.

In certain embodiments of the invention, the breast stabilizer for a cone beam breast tomographic imaging system has the receiver coupled to a patient interface panel of the cone beam tomographic imaging system through an adjustment mechanism.

In certain embodiments of the invention, the breast stabilizer for a cone beam breast tomographic imaging system has the receiver directly connected to a frame element of the cone beam tomographic imaging system while in certain embodiments of the invention, the breast stabilizer for a cone beam breast tomographic imaging system has the receiver coupled to a frame element of the cone beam tomographic imaging system through an adjustment mechanism.

In certain embodiments of the invention, the breast stabilizer for a cone beam breast tomographic imaging system has a receiver with a further coupling surface portion, and wherein the coupling of the body portion to the receiver of the cone beam tomographic imaging system comprises disposing the coupling surface portion in rotational frictional contact with the further coupling surface portion.

In certain embodiments of the invention, the coupling surface portion of the breast stabilizer for a cone beam breast tomographic imaging system has a further coupling surface portion having respective complementary interlocking elements and wherein the respective complementary interlocking elements are adapted to control a rotation of the body portion with respect to the receiver about a longitudinal axis of the body portion.

There are also embodiments of the invention in which the internal surface region comprises a portion of a substantially paraboloid surface region.

There are also embodiments of the invention in which the internal surface region comprises a portion of a substantially hyperboloid surface region.

There are also embodiments of the invention in which the internal surface region comprises a portion of a substantially hemispherical surface region.

In certain embodiments of the invention a method of stabilizing a breast for CBBCT scanning includes providing a CBBCT system that includes a CBBCT gantry and a frame element, providing a patient interface panel, the patient interface panel being supported by the frame element, the patient interface panel having a first patient interface surface region, the first patient interface surface region having an aperture therethrough. A receiver is provided, the receiver having a first coupling portion with a first coupling surface region and disposed in substantially fixed spatial relation to the aperture. A parameter of the breast is ascertained, and a breast stabilizer unit dimension identified based on the parameter of the breast. The identified breast stabilizer unit is provided, the breast stabilizer unit having an internal surface region corresponding to the parameter of the breast. The breast stabilizer unit has a second coupling portion with a second coupling surface region, the internal surface region being substantially immobile with respect to the coupling surface portion. The first coupling surface region is disposed in contact with the second coupling surface region thereby supporting the breast stabilizer unit with the receiver. The breast is disposed in contact with the internal surface region thereby supporting the breast with the breast stabilizer unit. The breast is then scanned with the CBBCT system.

In some embodiments of the invention, providing the breast stabilizer unit comprises selecting the breast stabilizer unit from a plurality of breast stabilizer units, while in other embodiments, providing the breast stabilizer unit comprises preparing an individualized breast stabilizer unit with an additive manufacturing process, and in some embodiments preparing the individualized breast stabilizer unit comprises forming the breast stabilizer unit with a molding process and in still further embodiments preparing the individualized breast stabilizer unit comprises forming the breast stabilizer unit with a wrapping process.

In certain embodiments of the invention, preparing the individualized breast stabilizer unit comprises forming the breast stabilizer unit with an additive manufacturing process including one or more of a 3D printing laser sintering process, a 3D printing photopolymer curing process, a 3D printing melt thermopolymer process, a 3D printing catalytic thermoset process, and combinations thereof.

In certain embodiments preparing the individualized breast stabilizer unit comprises forming the breast stabilizer unit with a subtractive process including one or more of a laser machining process, a mechanical milling process, an electrical discharge milling process, a chemical milling process, and combinations thereof.

In certain embodiments of the invention disposing the receiver in substantially fixed spatial relation to the aperture includes coupling the receiver to the patient interface panel.

In certain embodiments of the invention, the method of stabilizing a breast for CBBCT scanning comprises providing an adjustment device, coupling the adjustment device to the patient interface panel and coupling the receiver to the adjustment device.

In certain embodiments of the invention an adjustment device is provided that is coupled to the frame element and the receiver is coupled to the adjustment device.

In some embodiments of the invention, the adjustment device comprises a linear actuator.

In some embodiments of the invention, the linear actuator comprises a linear stepping motor.

In certain embodiments of the invention the linear actuator comprises a ballscrew assembly.

In some embodiments of the invention, the method of stabilizing a breast for CBBCT scanning comprises providing a CBBCT system, the CBBCT system includes a CBBCT gantry and a CBBCT frame element, providing a patient interface panel, the patient interface panel being supported by the frame element, the patient interface panel having a first patient interface surface region, the first patient interface surface region having an aperture therethrough, providing a receiver, the receiver being coupled in substantially fixed spatial relation to the aperture, the receiver having a first coupling portion with a coupling surface region. A spatial dimension of the breast is ascertained and a breast stabilizer unit prepared based on the breast dimension. The breast stabilizer unit has an internal surface region and a second coupling portion with a second coupling surface region, the internal surface region being substantially immobile with respect to the second coupling surface region. The first coupling surface region is disposed in contact with the second coupling surface region thereby supporting the breast stabilizer unit with the receiver, disposing the breast in contact with the internal surface region, thereby supporting the breast with the breast stabilizer unit. The CBBCT scanning of the breast is conducted with the CBBCT system.

While the exemplary embodiments described above have been chosen primarily from the field of apparatus, and corresponding systems and methods in the operation of a CBBCT imaging system, including breast stabilization systems and methods thereof, one of skill in the art will appreciate that the principles of the invention are equally well applied, and that the benefits of the present invention are equally well realized in a wide variety of other imaging technologies, for example, imaging of other body parts and imaging of other subjects such as industrial and technological products. Further, while the invention has been described in detail in connection with the presently preferred embodiments, it should be readily understood that the invention is not limited to such disclosed embodiments. Rather, the invention can be modified to incorporate any number of variations, alterations, substitutions, or equivalent arrangements not heretofore described, but which are commensu-

The invention claimed is:

1. A breast stabilizer for a cone beam breast tomographic imaging system comprising:
a body portion, said body portion having an internal surface region and a coupling surface portion, said internal surface region being substantially immobile with respect to said coupling surface portion, said internal surface region including a breast contact portion, said breast contact portion being adapted to support a corresponding surface region of a patient breast during operation of said cone beam tomographic imaging system, said coupling surface portion being adapted to couple said body portion to a receiver of said cone beam tomographic imaging system
wherein said receiver is coupled to a frame element of said cone beam tomographic imaging system through an adjustment mechanism.

2. A breast stabilizer for a cone beam breast tomographic imaging system as defined in claim 1 wherein said breast contact portion forms a substantially continuous circumferential surface region of said internal surface region.

3. A breast stabilizer for a cone beam breast tomographic imaging system as defined in claim 1 wherein said receiver is directly connected to a patient interface panel of said cone beam tomographic imaging system.

4. A breast stabilizer for a cone beam breast tomographic imaging system as defined in claim 1 wherein said receiver is integrally formed with a patient interface panel of said cone beam tomographic imaging system.

5. A breast stabilizer for a cone beam breast tomographic imaging system as defined in claim 1 wherein said receiver is coupled to a patient interface panel of said cone beam tomographic imaging system through an adjustment mechanism.

6. A breast stabilizer for a cone beam breast tomographic imaging system as defined in claim 1 wherein said receiver is directly connected to a frame element of said cone beam tomographic imaging system.

7. A breast stabilizer for a cone beam breast tomographic imaging system as defined in claim 1 wherein said receiver comprises a further coupling surface portion, and wherein said coupling said body portion to said receiver of said cone beam tomographic imaging system comprises disposing said coupling surface portion in rotational frictional contact with said further coupling surface portion.

8. A breast stabilizer for a cone beam breast tomographic imaging system as defined in claim 1 wherein said internal surface region comprises a portion of a substantially paraboloid surface region.

9. A breast stabilizer for a cone beam breast tomographic imaging system as defined in claim 1 wherein said internal surface region comprises a portion of a substantially hyperboloid surface region.

10. A breast stabilizer for a cone beam breast tomographic imaging system as defined in claim 1 wherein said internal surface region comprises a portion of a substantially hemispherical surface region.

11. A breast stabilizer for a cone beam breast tomographic imaging system as defined in claim 7 wherein said coupling surface portion and said further coupling surface portion have respective complementary interlocking elements and wherein said respective complementary interlocking elements are adapted to control a rotation of said body portion with respect to said receiver about a longitudinal axis of said body portion.

12. A method of stabilizing a breast for Cone Beam Breast Computed Tomography (CBBCT) scanning comprising:
providing a CBBCT system, said CBBCT system including a CBBCT gantry and a frame element;
providing a patient interface panel, said patient interface panel being supported by said frame element, said patient interface panel having a first patient interface surface region, said first patient interface surface region having an aperture therethrough;
providing a receiver, said receiver having a first coupling portion with a first coupling surface region;
disposing said receiver in substantially fixed spatial relation to said aperture;
ascertaining a parameter of said breast;
identifying a breast stabilizer unit dimension based on said parameter of said breast;
providing said identified breast stabilizer unit, said breast stabilizer unit having an internal surface region corresponding to said parameter of said breast, said breast stabilizer unit having a second coupling portion with a second coupling surface region;
said internal surface region being substantially immobile with respect to said second coupling portion;
disposing said first coupling surface region in contact with said second coupling surface region, and thereby supporting said breast stabilizer unit with said receiver;
disposing said breast in contact with said internal surface region, and thereby supporting said breast with said breast stabilizer unit;
scanning said breast with said CBBCT system;
providing an adjustment device;
coupling said adjustment device to said patient interface panel; and
coupling said receiver to said adjustment device.

13. A method of stabilizing a breast for Cone Beam Breast Computed Tomography (CBBCT) scanning as defined in claim 12 wherein said adjustment device comprises a linear actuator.

14. A method of stabilizing a breast for Cone Beam Breast Computed Tomography (CBBCT) scanning as defined in claim 13 wherein said linear actuator comprises a linear stepping motor.

15. A method of stabilizing a breast for Cone Beam Breast Computed Tomography (CBBCT) scanning as defined in claim 13 wherein said linear actuator comprises a ballscrew assembly.

16. A method of stabilizing a breast for Cone Beam Breast Computed Tomography (CBBCT) scanning comprising:
providing a CBBCT system, said CBBCT system including a CBBCT gantry and a CBBCT frame element;
providing a patient interface panel, said patient interface panel being supported by said frame element, said patient interface panel having a first patient interface surface region, said first patient interface surface region having an aperture therethrough;
providing a receiver, said receiver being coupled in substantially fixed spatial relation to said aperture, said receiver having a first coupling portion with a first coupling surface region;
ascertaining a spatial dimension of said breast;
preparing a breast stabilizer unit based on said spatial dimension said breast stabilizer unit having an internal surface region and a second coupling portion with a second coupling surface region, said internal surface region being substantially immobile with respect to said second coupling surface region;
disposing said first coupling surface region in contact with said second coupling surface region and thereby supporting said breast stabilizer unit with said receiver;
disposing said breast in contact with said internal surface region and thereby supporting said breast with said breast stabilizer unit; and
conducting said CBBCT scanning of said breast with said CBBCT system.

* * * * *